United States Patent
Zhan et al.

(10) Patent No.: US 9,586,946 B2
(45) Date of Patent: Mar. 7, 2017

(54) SELECTIVE IMMUNOPROTEASOME INHIBITORS WITH NON-PEPTIDE SCAFFOLDS

(71) Applicant: University of Kentucky Research Foundation, Lexington, KY (US)

(72) Inventors: Chang-Guo Zhan, Lexington, KY (US); Kyung Bo Kim, Lexington, KY (US); Vinod Kasam, Lexington, KY (US); Na-Re Lee, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 15/155,627

(22) Filed: May 16, 2016

(65) Prior Publication Data

US 2016/0332998 A1     Nov. 17, 2016

Related U.S. Application Data

(60) Provisional application No. 62/162,324, filed on May 15, 2015.

(51) Int. Cl.
*C07D 405/14*     (2006.01)

(52) U.S. Cl.
CPC .................. *C07D 405/14* (2013.01)

(58) Field of Classification Search
None
See application file for complete search history.

(56) References Cited

PUBLICATIONS

Kasam et al. Bioorganic & Medicinal Chemistry Letters, (2014), 24(15), p. 3614-3617 (disclosed in IDS).*
W. Porter Pure & Appl Chem, (1991), 63(8), p. 1119-1122.*
Li et al. Encyclopedia of Chemical Processing (2006) p. 449-458.*
Norman et al Bioorg. & Med. Chem. (2013), 21(17), 5548-5560, and supplementary material.*
Kisselev, et al.; Proteasome inhibitors: from research tools to drug candidates; Chem. Biol. 2001, 8, 739.
Richardson, et al.; A Phase 2 Study of Bortezomib in Relapsed, Refractory Myeloma; Engl. J. Med. 2003, 348, 609-2617.
Kasam, et al., Selective immunoproteasome inhibitors with non-peptide scaffolds identified from structure-based virtual screening; Bioorg Med Chem Lett. 2014, 24(15): 3614-7.

* cited by examiner

*Primary Examiner* — Yong Chu
(74) *Attorney, Agent, or Firm* — Stites & Harbison, PLLC; Mandy Wilson Decker

(57) ABSTRACT

Compounds useful for inhibiting the immunoproteasome have the formula of

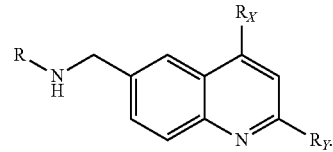

Methods and compounds for inhibiting the immunoproteasome, particularly, immunoproteasome inhibitors with non-peptide scaffolds, are described.

13 Claims, 2 Drawing Sheets

SELECTIVE IMMUNOPROTEASOME INHIBITORS WITH NON-PEPTIDE SCAFFOLDS

RELATED APPLICATIONS

This application claims priority from U.S. Provisional Application Ser. No. 62/162,324 filed May 15, 2015, the entire disclosure of which is incorporated herein by this reference.

GOVERNMENT INTEREST

This invention was made with government support under RC1MH088480 and R01CA128903 awarded by the National Institutes of Health. The government has certain rights in the invention.

TECHNICAL FIELD

The presently-disclosed subject matter relates to inhibition of the immunoproteasome. In particular, the presently-disclosed subject matter relates to immunoproteasome inhibitors with non-peptide scaffolds.

INTRODUCTION

Proteasome plays a central role in maintaining cellular homeostasis, controlling the cell cycle, removing misfolded proteins that can be toxic, and regulating the immune system.[1] This crucial protein degradation machinery has been implicated in multiple diseases such as Alzheimer's disease, Huntington's disease (HD), inflammatory bowel diseases (IBD), autoimmune diseases, multiple myeloma (MM) and other cancers.[2] In particular, proteasome has been recognized as a promising cancer target, and the Food and Drug Administration (FDA) has approved proteasome inhibitors bortezomib (Velcade®) in 2003 and carfilzomib (Kyprolis®) in 2012 for the MM treatment. The FDA approvals of these proteasome inhibitors as chemotherapeutic agents have dramatically improved the therapeutic landscape for patients with MM.[3]

Despite the remarkable successes of these proteasome inhibitors in the clinic, intrinsic and acquired drug resistance remains a major clinical challenge. Inhibitors that are peptide backbone-based also have relatively short half-lives when administered to a subject. In addition, these drugs have failed to provide clinical benefit to patients with solid cancers,[4-6] further highlighting the need for next-generation of proteasome inhibitors.

There are two main proteasome subtypes: the constitutive proteasome (CP) which is expressed in all eukaryotic cells and the immunoproteasome (IP) which is expressed in immune cells and can be induced in other cell types. Constitutive proteasome contains three catalytic subunits denoted as 31, 32, and 35, whereas the three corresponding catalytic subunits of immunoproteasome are denoted as 31i, 32i, and 35i. The catalytic subunits responsible for the chymotrypsin-like (CT-L) activity (35 and 35i) are thought to be most physiologically important and have been recognized as the key targets of bortezomib and carfilzomib.[7,8] However, these drugs have failed to achieve efficacy in patients with solid cancers despite strong indications of activity in preclinical animal models. The failure of these drugs has been attributed to their poor metabolic stability.[9] Further, recent reports revealed the importance of targeting the immunoproteasome catalytic subunit 35i in killing cancer cells.[8]

Therefore, it is highly desirable to identify unique compounds with non-peptide scaffolds that can selectively inhibit the immunoproteasome 35i.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

As noted hereinabove, it is highly desirable to identify unique, immunoproteasome-selective inhibitors with non-peptide scaffolds.

Through combined virtual screening and experimental studies targeting the immunoproteasome, the present inventors have identified a set of immunoproteasome inhibitors with diverse non-peptide scaffolds. Some of the identified inhibitors have significant selectivity for the immunoproteasome over the constitutive proteasome. Unlike most of the currently available proteasome inhibitors, these new inhibitors lacking electrophilic pharmacophores are not contemplated to form a covalent bond with proteasome after the binding. These non-peptide scaffolds are useful for targeting the immunoproteasome.

The presently-disclosed subject matter includes compounds, compositions, and methods useful for inhibiting immunoproteasome. The presently-disclosed inhibitors are compounds have non-peptide scaffolds. In some embodiments, the compound has the structure of the formula (I):

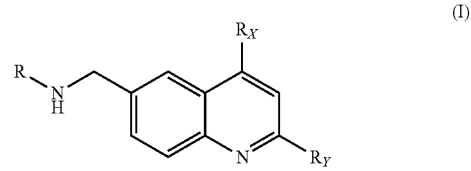

In some embodiments of the compound of formula (I) the compound has the structure of formula (IA):

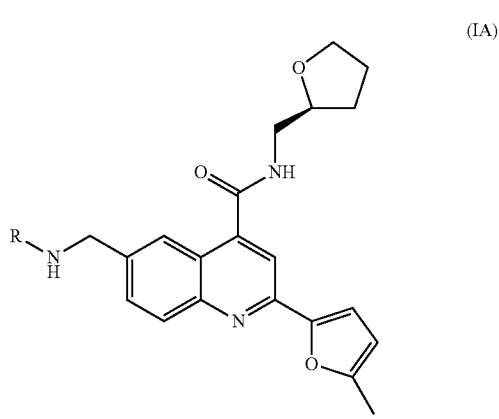

In some embodiments of the compound of formula (I) the compound has the structure of formula (IB):

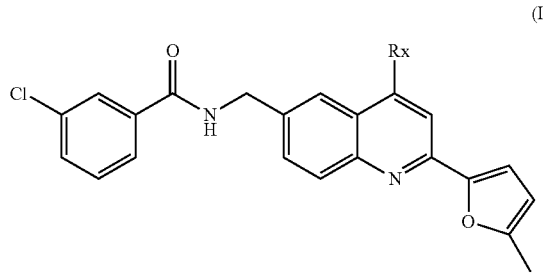
(IB)

In some embodiments, the compound has the structure of the formula (II):

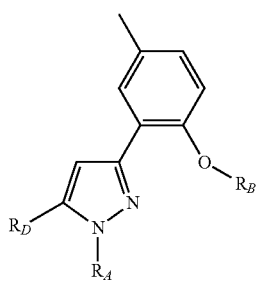
(II)

The presently-disclosed subject matter includes compositions that include a compound as described herein. In some embodiments the composition includes a compound of formula (I) or a pharmaceutically-acceptable salt thereof. In some embodiments the composition includes a compound of formula (II) or a pharmaceutically-acceptable salt thereof. In some embodiments the composition includes a compound selected from compounds 1-19, or a pharmaceutically-acceptable salt thereof, as set forth in Table 1B.

The presently-disclosed subject matter includes methods of inhibiting immunoproteasome activity. In some embodiments a method of inhibiting immunoproteasome activity involves administering a compound or a composition as described herein. In some embodiments a method of inhibiting immunoproteasome activity involves administering a compound of formula (I), or a composition comprising a compound of formula (I) or a pharmaceutically-acceptable salt thereof. In some embodiments a method of inhibiting immunoproteasome activity involves administering a compound of formula (II), or a composition comprising a compound of formula (II) or a pharmaceutically-acceptable salt thereof. In some embodiments a method of inhibiting immunoproteasome activity involves administering a compound selected from compounds 1-19, or a composition comprising a compound selected from compounds 1-19 or a pharmaceutically-acceptable salt thereof, as set forth herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
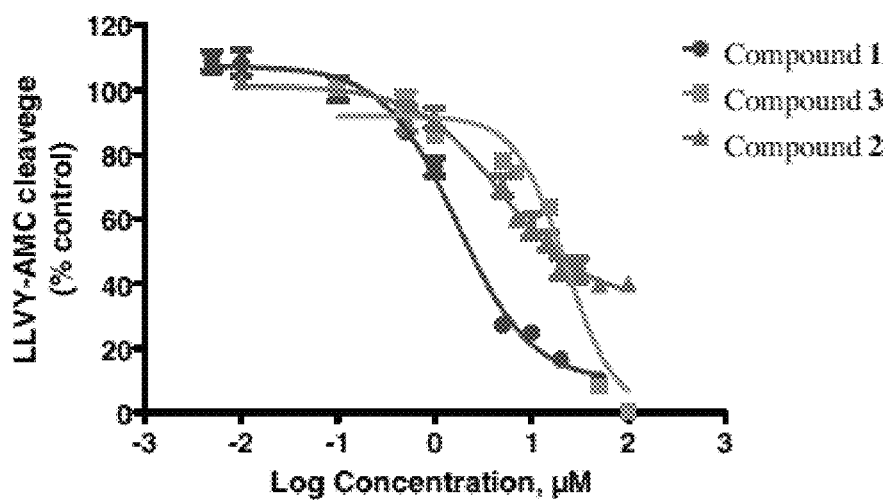
FIG. 1. Dose-dependent inhibition of the immunoproteasome CT-L activity (initial velocity) by compounds 1-3: plots of the remaining CT-L activity versus the inhibitor concentration.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds, compositions, and methods useful for inhibiting immunoproteasome. The presently-disclosed inhibitors are compounds have non-peptide scaffolds. In some embodiments, the compound has the structure of the formula (I):

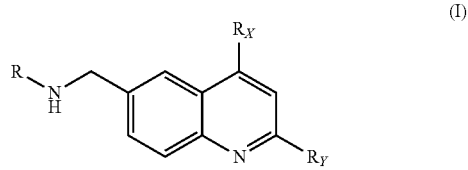
(I)

wherein R can be

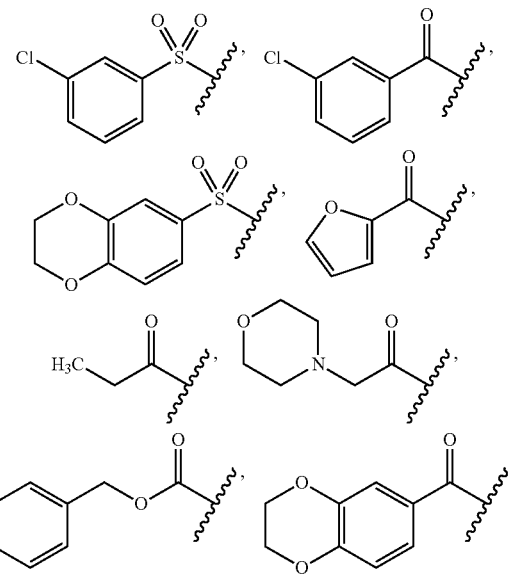

-continued
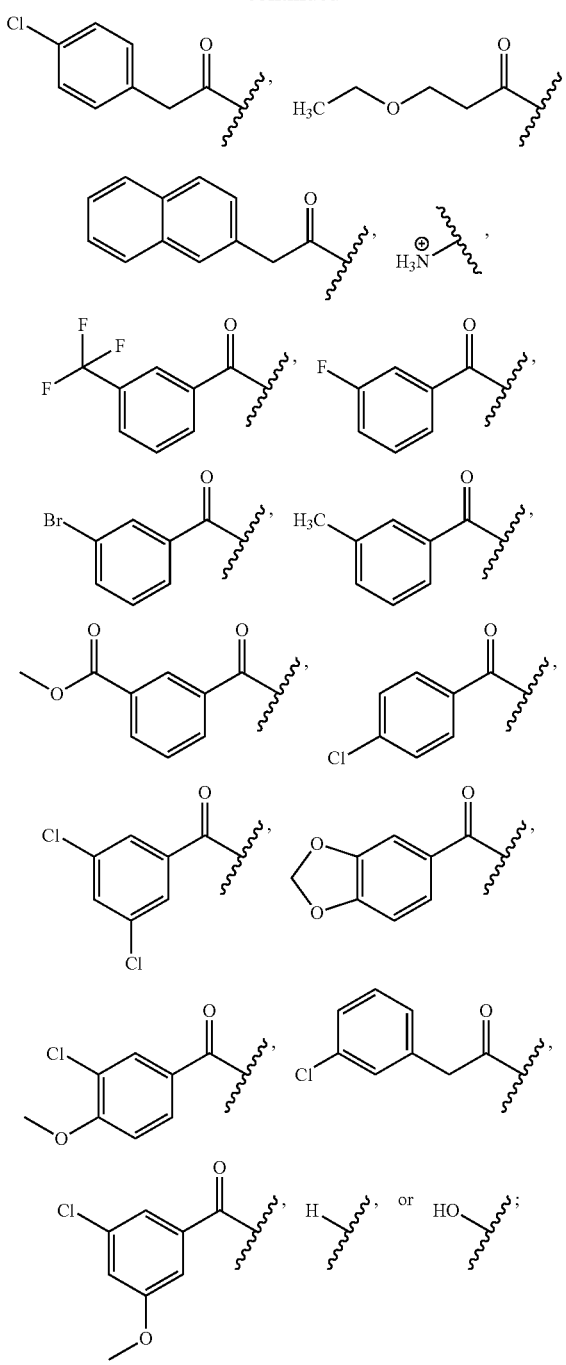
$R_X$ can be
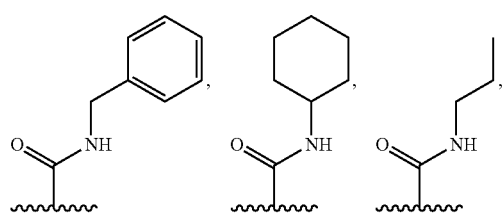
-continued
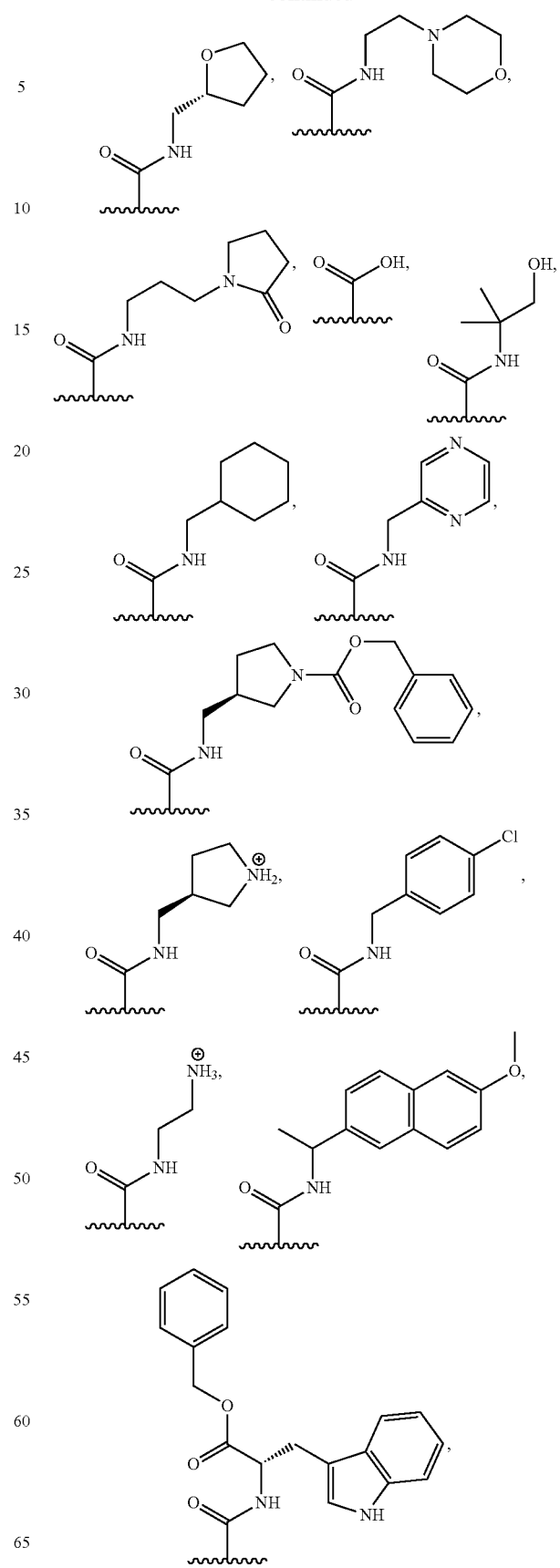

-continued
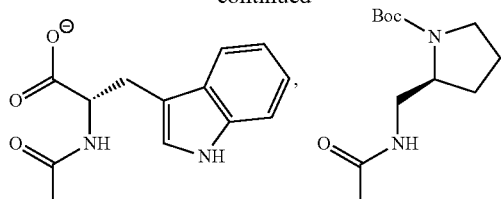
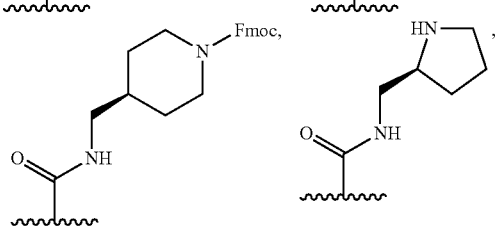
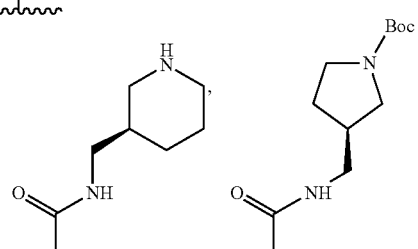
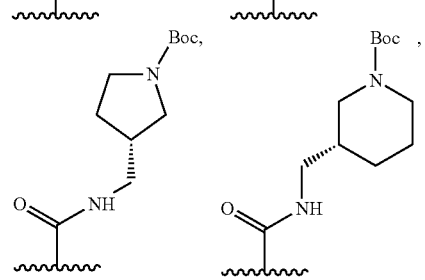
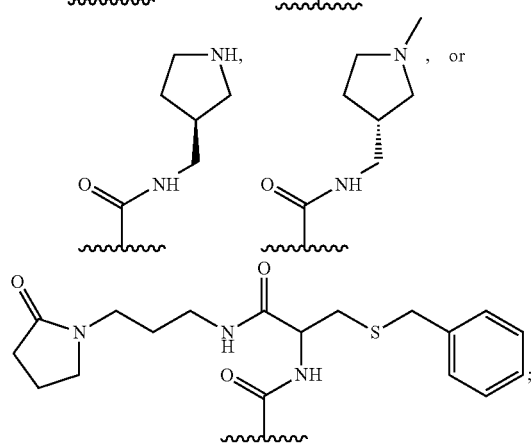
$R_Y$ can be
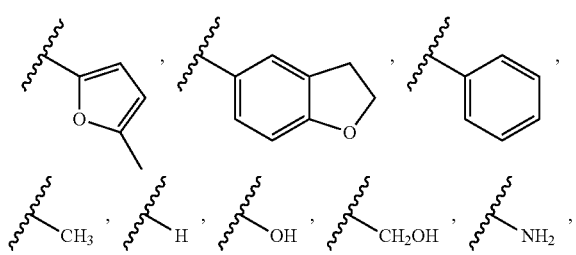
-continued
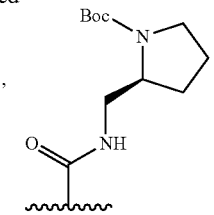
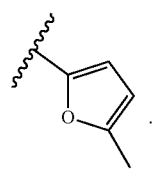 [SMILES: *c1ccc(C)o1]
In some embodiments of the compound of formula (I), $R_Y$ is
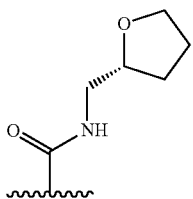
In some embodiments of the compound of formula (I), $R_X$ is
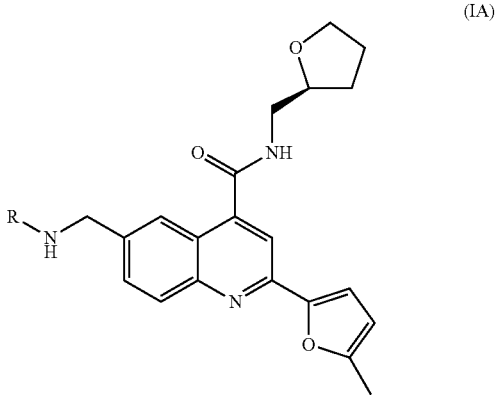
In some embodiments of the compound of formula (I) the compound has the structure of formula (IA):
(IA)
wherein R is selected from the group consisting of
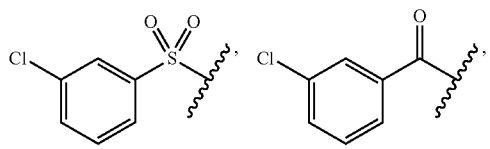

-continued
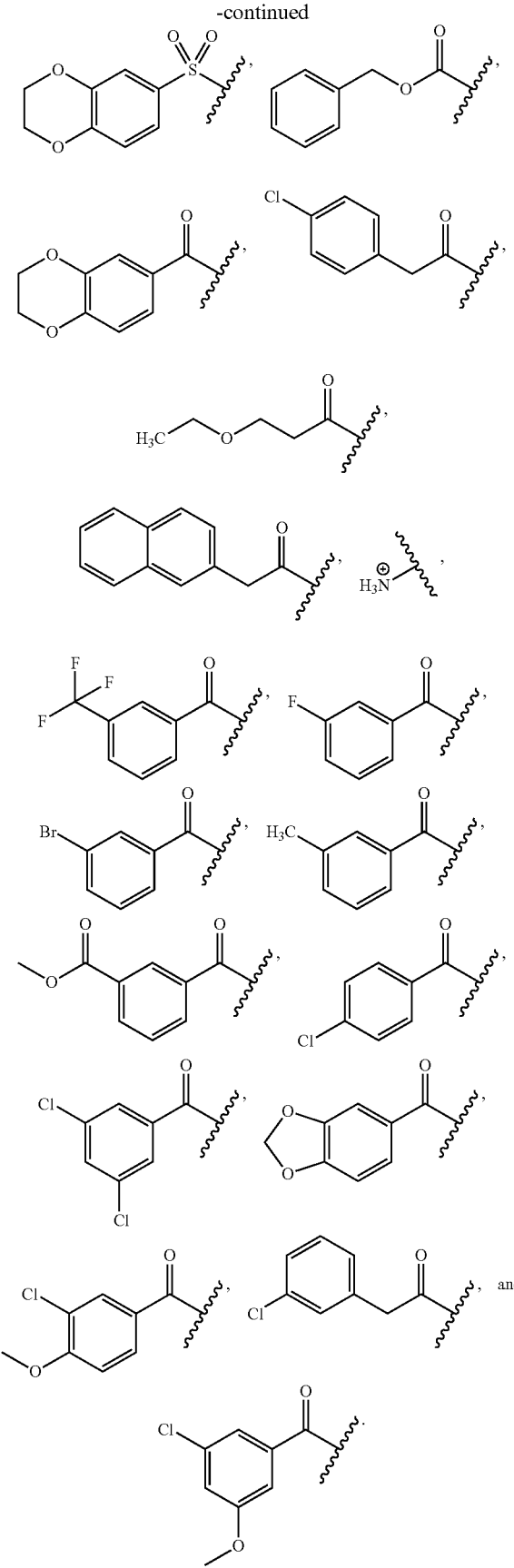
In some embodiments of the compound of formula (I), R is
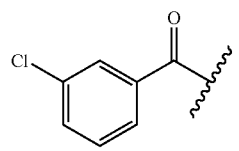
In some embodiments of the compound of formula (I) the compound has the structure of formula (IB):

-continued
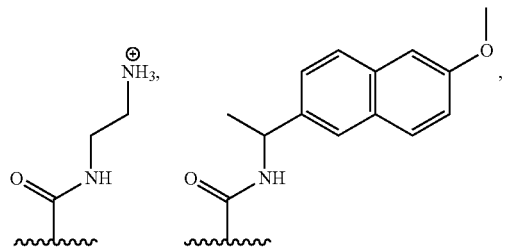
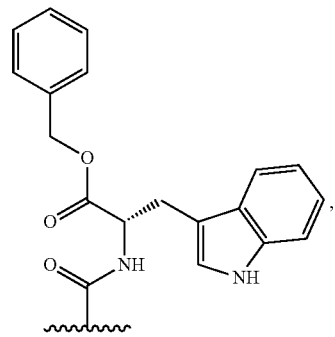
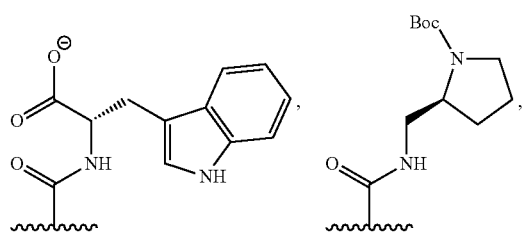
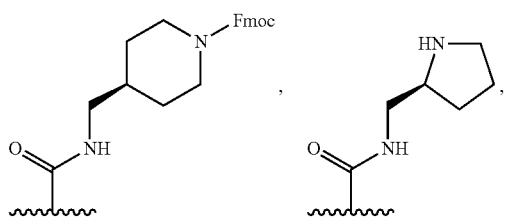
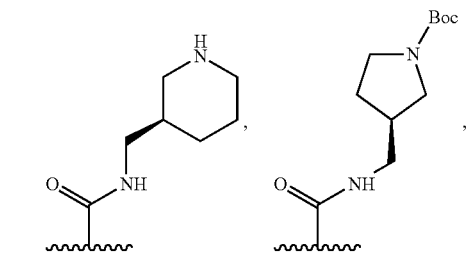
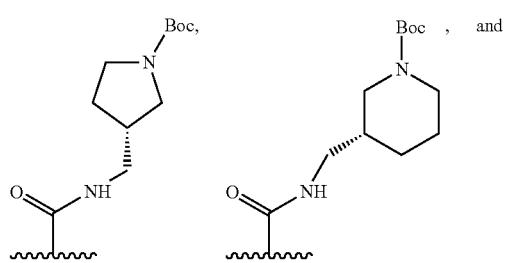
-continued
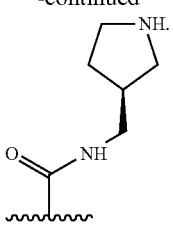
wherein $R_X$ is selected from the group consisting of
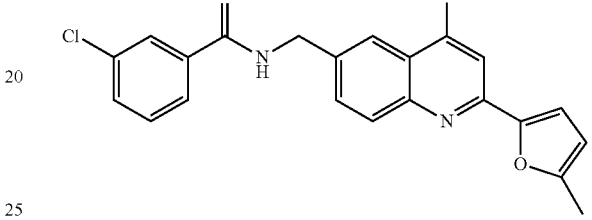
(IB)
In some embodiments of the compound of formula (I) the compound has the structure of formula (IB) wherein $R_X$ is selected from the group consisting of
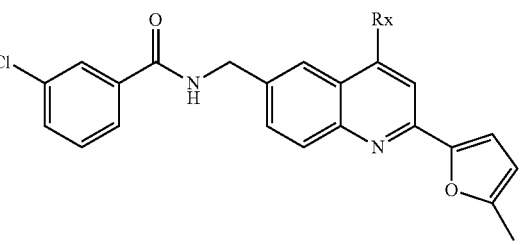
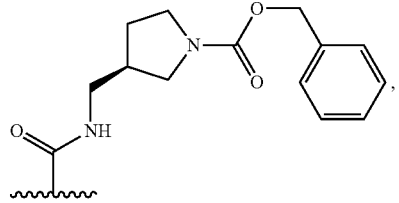
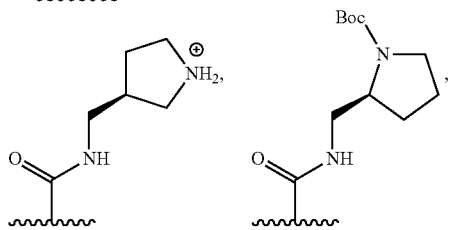
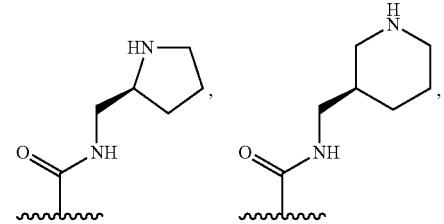
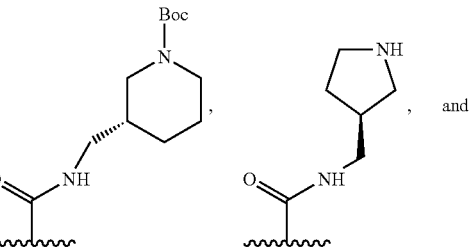

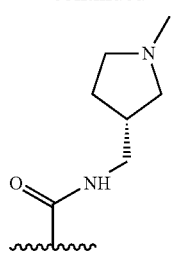

In some embodiments of the compound of formula (I) the compound has the structure of formula (IB) wherein $R_X$ is selected from the group consisting of

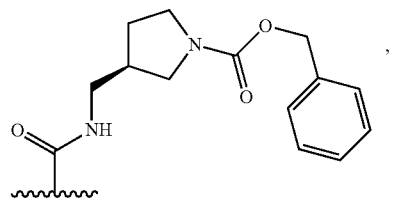

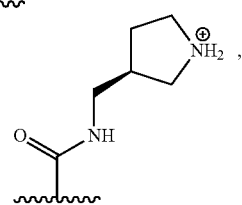

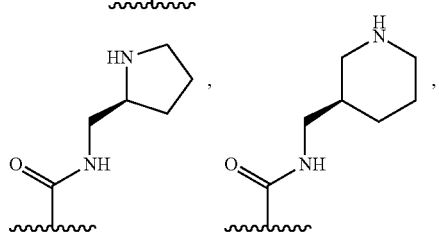

In some embodiments of the compound of formula (I) the compound has the structure of formula (IB) wherein $R_X$ is

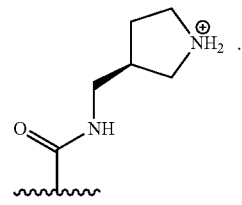 [SMILES: *C(=O)NC[C@H]1CC[NH2+]C1]

In some embodiments of the compound of formula (I) the compound has the structure of formula (IB) wherein $R_X$ is

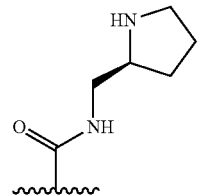 [SMILES: *C(=O)NC[C@@H]1CCCN1]

In some embodiments of the compound of formula (I) the compound has the structure of formula (IB) wherein $R_X$ is

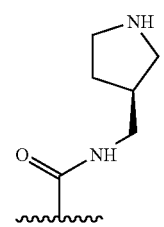

In some embodiments of the compound of formula (I) the compound has the structure of formula (IB) wherein $R_X$ is

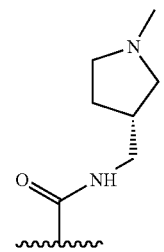

In some embodiments, the compound has the structure of the formula (II):

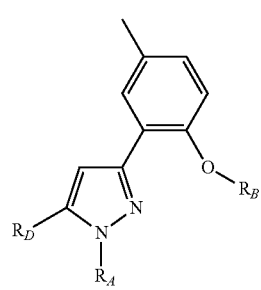

(II)

wherein $R_A$ can be

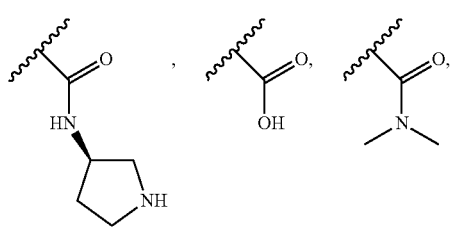

-continued
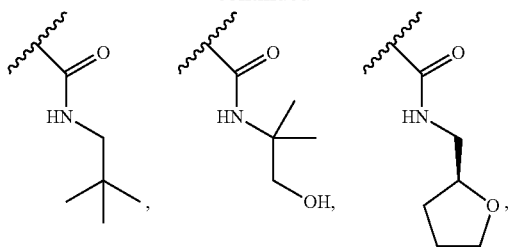
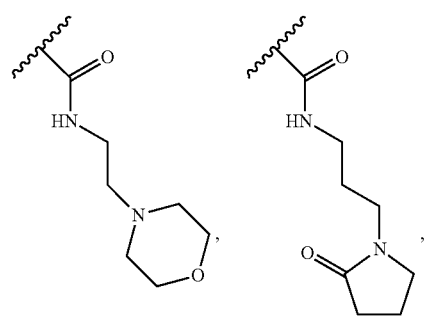
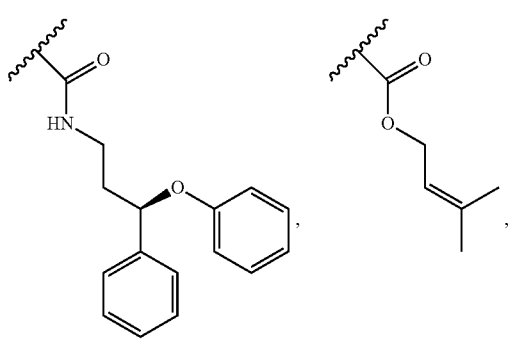
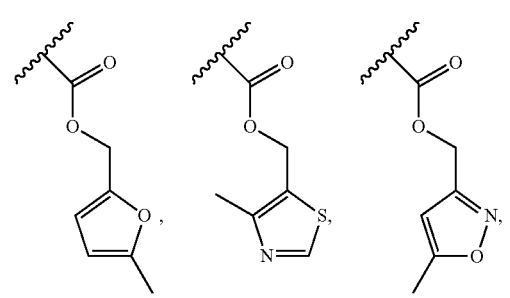
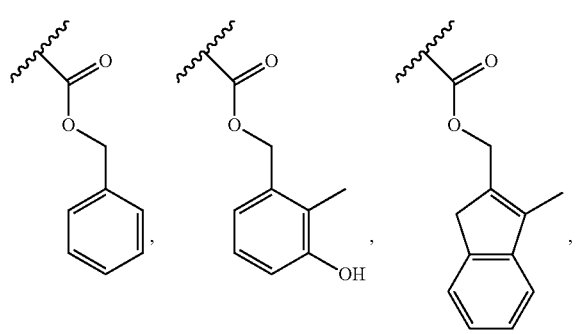
-continued
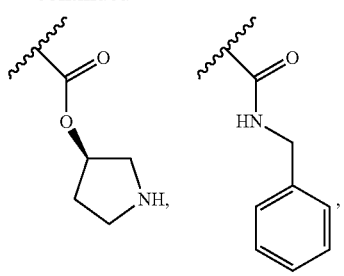
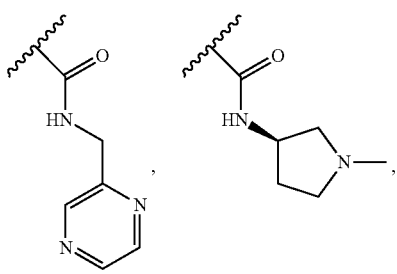
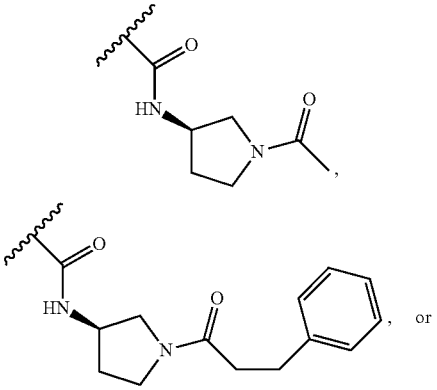
, or
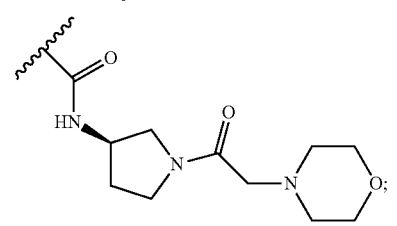
$R_B$ can be
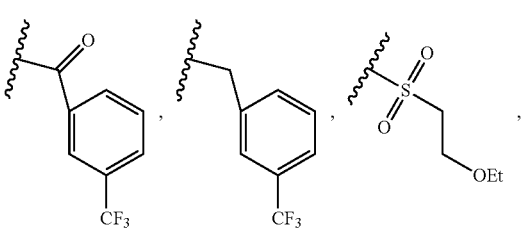
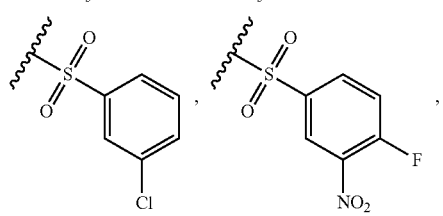

-continued

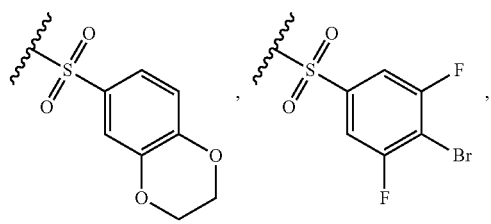

$R_D$ can be

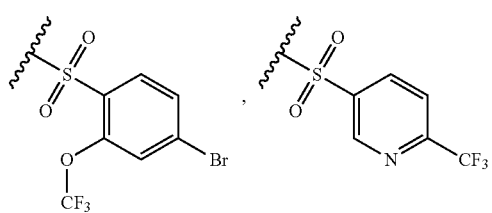

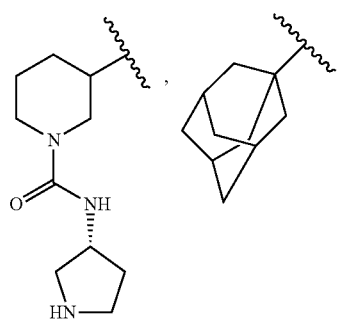

tion includes a compound of formula (II) or a pharmaceutically-acceptable salt thereof. In some embodiments the composition includes a compound selected from compounds 1-19, or a pharmaceutically-acceptable salt thereof:

1

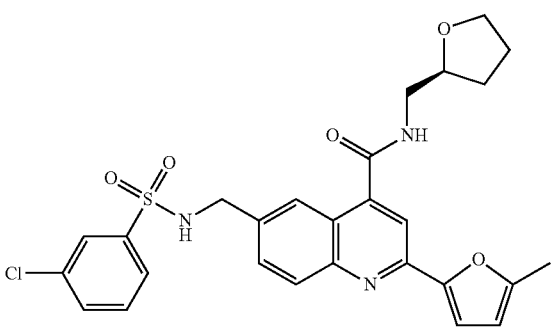

2

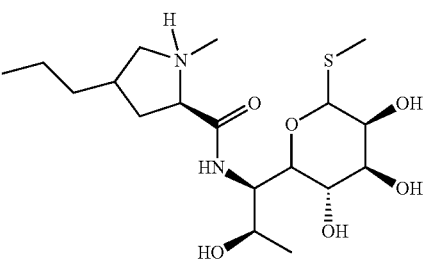

3

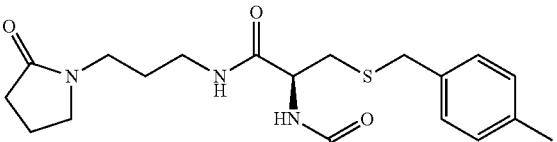

4

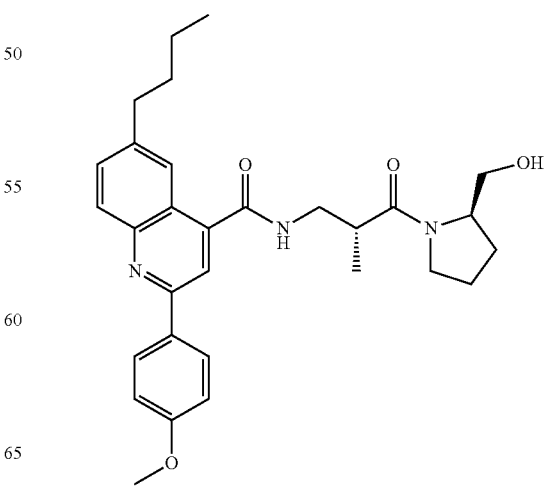

As noted herein above, the presently-disclosed subject matter includes compositions that include a compound as described herein. In some embodiments the composition includes a compound of formula (I) or a pharmaceutically-acceptable salt thereof. In some embodiments the composi- -continued
5
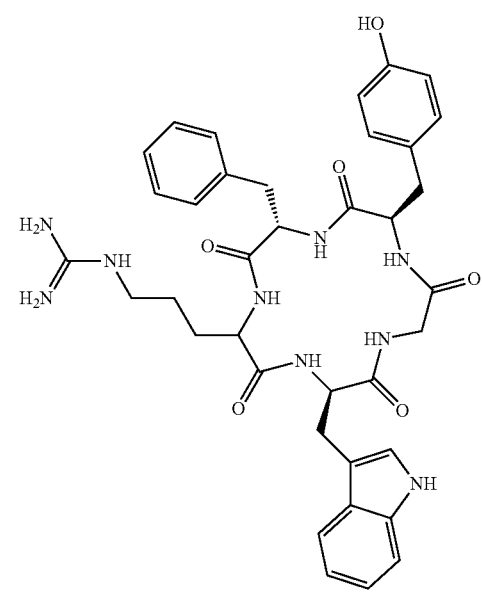
6
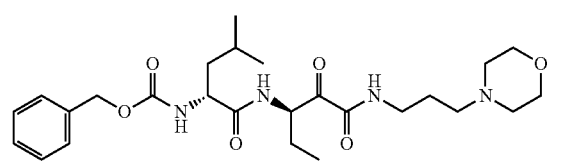
7
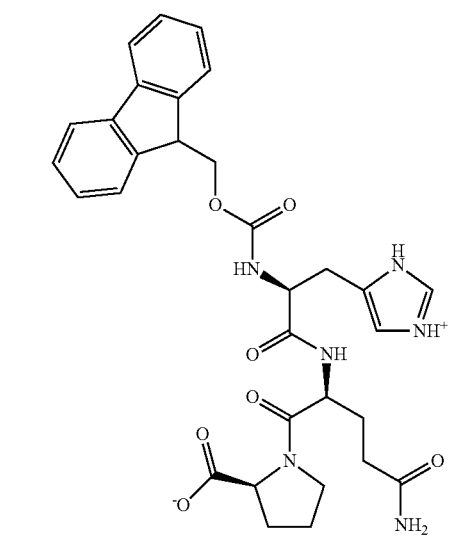
8
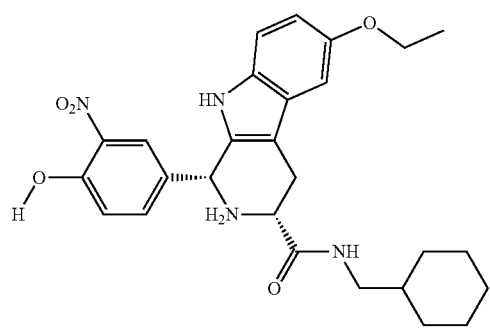
-continued
9
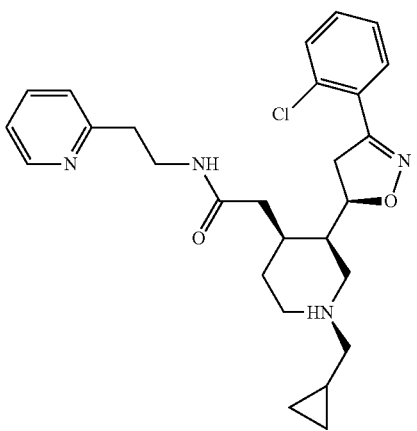
10
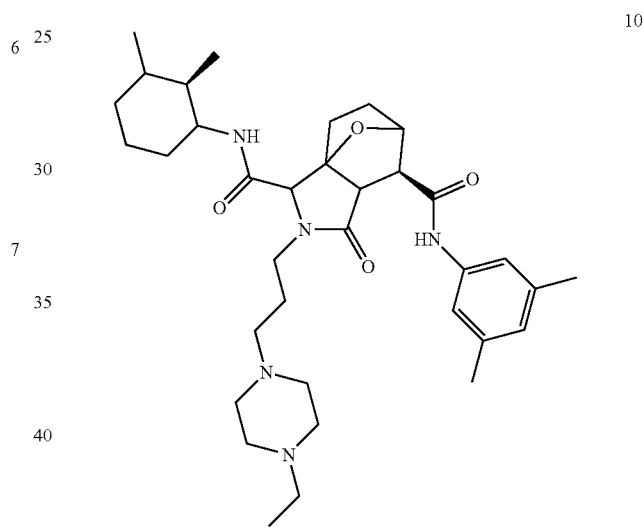
11
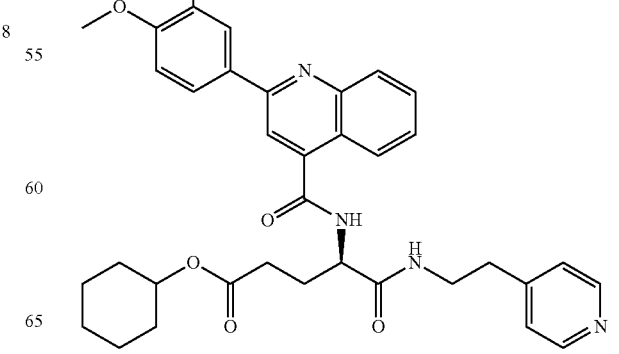

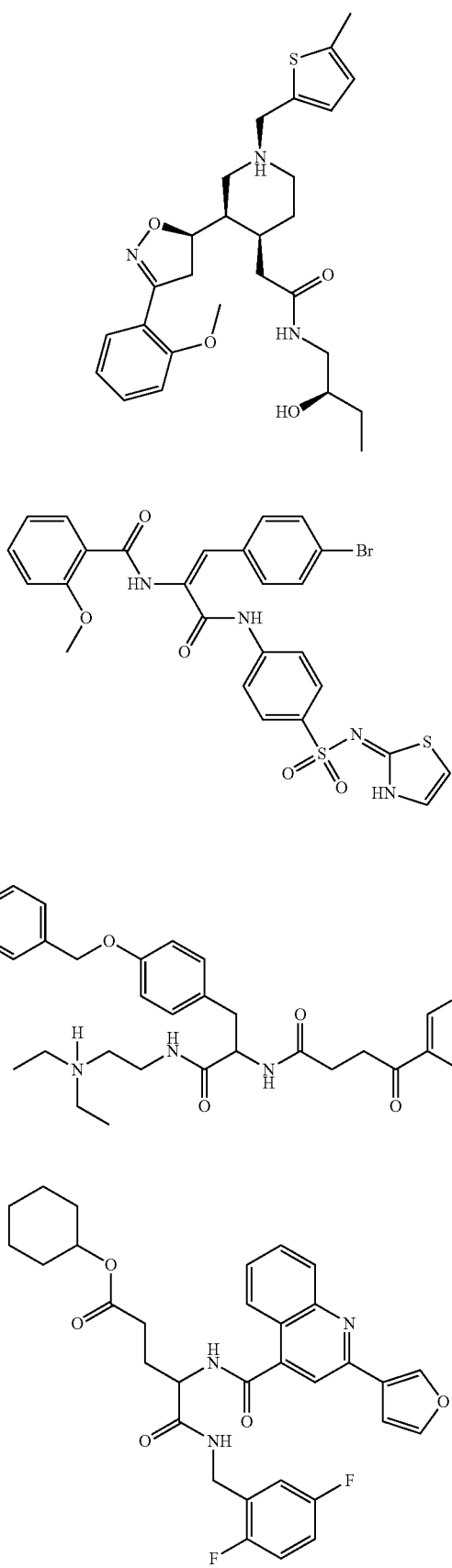
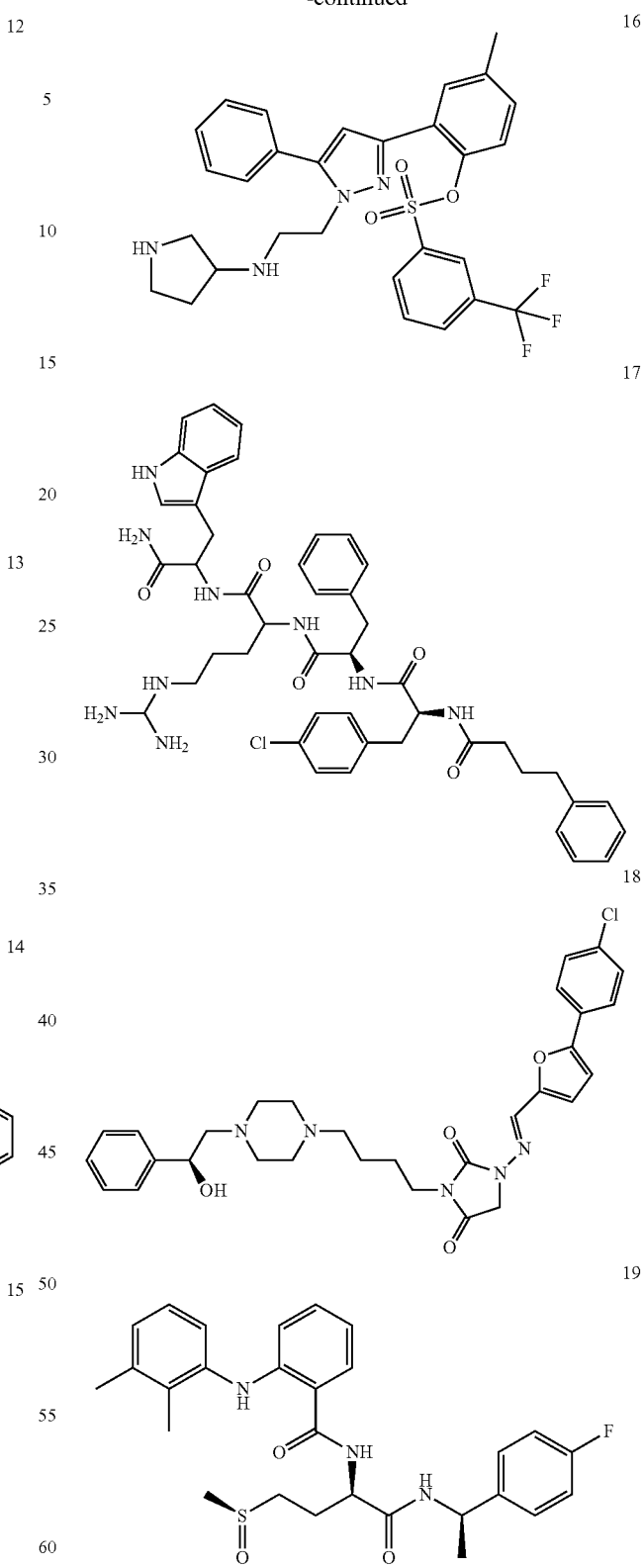
Compositions of the presently-disclosed subject matter can further include a pharmaceutically-acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As noted herein above, the presently-disclosed subject matter includes methods of inhibiting immunoproteasome activity and methods of selectively inhibit the immunoproteasome 35i. In some embodiments a method of inhibiting immunoproteasome activity involves administering a compound or a composition as described herein. In some embodiments a method of inhibiting immunoproteasome activity involves administering a compound of formula (I), or a composition comprising a compound of formula (I) or a pharmaceutically-acceptable salt thereof. In some embodiments a method of inhibiting immunoproteasome activity involves administering a compound of formula (II), or a composition comprising a compound of formula (II) or a pharmaceutically-acceptable salt thereof. In some embodiments a method of inhibiting immunoproteasome activity involves administering a compound selected from compounds 1-19, or a composition comprising a compound selected from compounds 1-19 or a pharmaceutically-acceptable salt thereof, as set forth herein.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one compound and/or composition provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

In some embodiments of the presently-disclosed subject matter, the inhibitor is administered in vitro or in a cultured cell.

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

In some embodiments of the presently-disclosed subject matter, the immunoproteasome inhibition can be useful for treating a cancer or other condition, such as Alzheimer's disease, Huntington's disease (HD), inflammatory bowel diseases (IBD), autoimmune diseases, or multiple myeloma (MM).

As used herein, the terms "treatment" or "treating" relate to any treatment of a condition, including but not limited to prophylactic treatment to prevent development or reduce severity of a disorder. The terms "treatment" or "treating" include: (1) preventing a condition from occurring in a subject who may be predisposed to the; (2) inhibiting the condition, i.e., arresting their development; (3) ameliorating or relieving the symptoms of the condition; and (4) causing regression of the condition.

As will be recognized by one of ordinary skill in the art, the term "inhibiting" or "inhibition" does not refer to the ability to completely inactivate all target biological activity in all cases. Rather, the skilled artisan will understand that the term "inhibiting" refers to decreasing biological activity of a target. Such decrease in biological activity can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Disclosed herein are non-peptide scaffolds of selective inhibitors of the immunoproteasome. Exemplary inhibitors are set forth in these Examples.

Virtual Screening

As disclosed herein, exemplary compounds including diverse non-peptide scaffolds, which were identified through combined virtual screening and experimental studies targeting the catalytic subunit 35i (which is also known as LMP7).

The virtual screening was based on the present inventors' previously-modeled three-dimensional (3D) structure of the immunoproteasome,[10-12] and performed on a compound library at Genomics Research Institute (GM), the University of Cincinnati (UC). The UC/GRI compound library containing structural information for about 300,000 compounds was provided by Procter & Gamble (P&G) and belonged to a consortium including the University of Kentucky as a member.

The virtual screening procedure utilized to screen the chemical compound library is essentially similar to that which the present inventors used to identify small-molecule inhibitors of other proteins.[13,14] The 300,000 compounds were first screened by using a structure-based virtual screening approach,[13,15] leading to identification of top-25,000 compounds. The subsequent energy-minimization and Molecular Mechanics/Generalized Born Surface Area (MM/GBSA) binding energy calculations using Amberg software[16] led to identification of the top-1000 compounds. Further structural analysis on possible interactions with key amino-acid residues (including Thr1, Ser21, Ser27, Gly47, Ala49, and Asp324) led to selection of the top-130 compounds that could inhibit the immunoproteasome.

Testing Inhibitory Activity

The computationally selected 13 compounds were tested for their inhibitory activity against the CT-L activity of the immunoproteasome. The identified active compounds were also tested for their inhibitory activity against the CT-L activity of the constitutive proteasome. For the initial activity screening, the selected compounds were dissolved in DMSO and used at a concentration of 5 μM. Epoxomicin (1 tM), which reached the 100% inhibition, was used as a positive control. 20S human immunoproteasome and constitutive proteasome (Boston Biochem) were 2-fold diluted in an assay buffer (20 mM Tris/Cl, pH 8.0, 0.5 mM EDTA, 0.035% SDS).[17]

Specifically, selected compounds were preincubated with 50 ng/well of the immunoproteasome or constitutive proteasome in a 96-well plate at room temperature for 13 min. 100 µM of Suc-LLVY-AMC, a fluorogenic peptide substrate for the CT-L activity, was then added to the wells. Fluorogenic signals of the free AMC (Ex: 360, Em: 460)[18] were recorded for 90 min. The initial reaction velocities (RFU/min) of each compound were calculated as a percentage of the positive control. All enzyme activity assays were carried out in triplicate.

Inhibitor Selectivity

According to the activity assays, nine of the tested compounds (1-19) showing the significant inhibition against the immunoproteasome are listed in Table 1A for their activity data and depicted in Table 1B for their molecular structures. The hit rate of the virtual screening was 10%. Based on the activity data in Table 1A, compounds 1-3 at 5 µM inhibited the CT-L activity of the immuno-proteasome by about 36-85%, whereas these compounds at 5 inhibited the constitutive proteasome by only 2-20%.

This indicates that compounds 1-3 are highly selective inhibitors for the immunoproteasome. In particular, compounds 1 and 3 at 5 µM inhibited the immunoproteasome by 85-62%, respectively. These most potent two compounds, along with compound 2, were tested further for the dose-dependent inhibition (FIG. 1) in order to determine their $IC_{50}$ values (Table 1A) against the immunoproteasome. As shown in Table 1A, the $IC_{50}$ values for compounds 1 to 3 are 1.7, 22, and 4.9 respectively. These compounds, particularly compounds 1 and 3, are promising immunoproteasome inhibitors with non-peptide scaffolds.

TABLE 1A

The inhibitory activities of the identified 19 compounds against immunoproteasome (IP) and constructive proteasome (CP) - their activities for substrate epoxomicin (1 µM). The inhibitory activities were characterized as the remaining enzyme activity (%) in the presence of the inhibitor at 5 µM.

| Compound (of Table 1B) | % IP activity $(IC_{50})^{a,b}$ | % CP activity[a] |
|---|---|---|
| 1 | 15 (1.7 µM) | 80 |
| 2 | 64 (22 µM) | 98 |
| 3 | 38 (4.9 µM) | 85 |
| 4 | 79 | 98 |
| 5 | 81 | 82 |
| 6 | 86 | 94 |
| 7 | 65 | 76 |
| 8 | 90 | 106 |
| 9 | 87 | 86 |
| 10 | 82 | 85 |
| 11 | 80 | 80 |
| 12 | 69 | 72 |
| 13 | 91 | 88 |
| 14 | 70 | 76 |
| 15 | 74 | 80 |
| 16 | 42 | 50 |
| 17 | 42 | 41 |
| 18 | 75 | 84 |
| 19 | 69 | 67 |

[a]The remaining activity (%) of the enzyme in the presence of the inhibitor at 5 µM.
[b]The determined $IC_{50}$ values are given in parentheses.

TABLE 1B

Structures of the identified 19 compounds against immunoproteasome (IP) and constructive proteasome (CP).

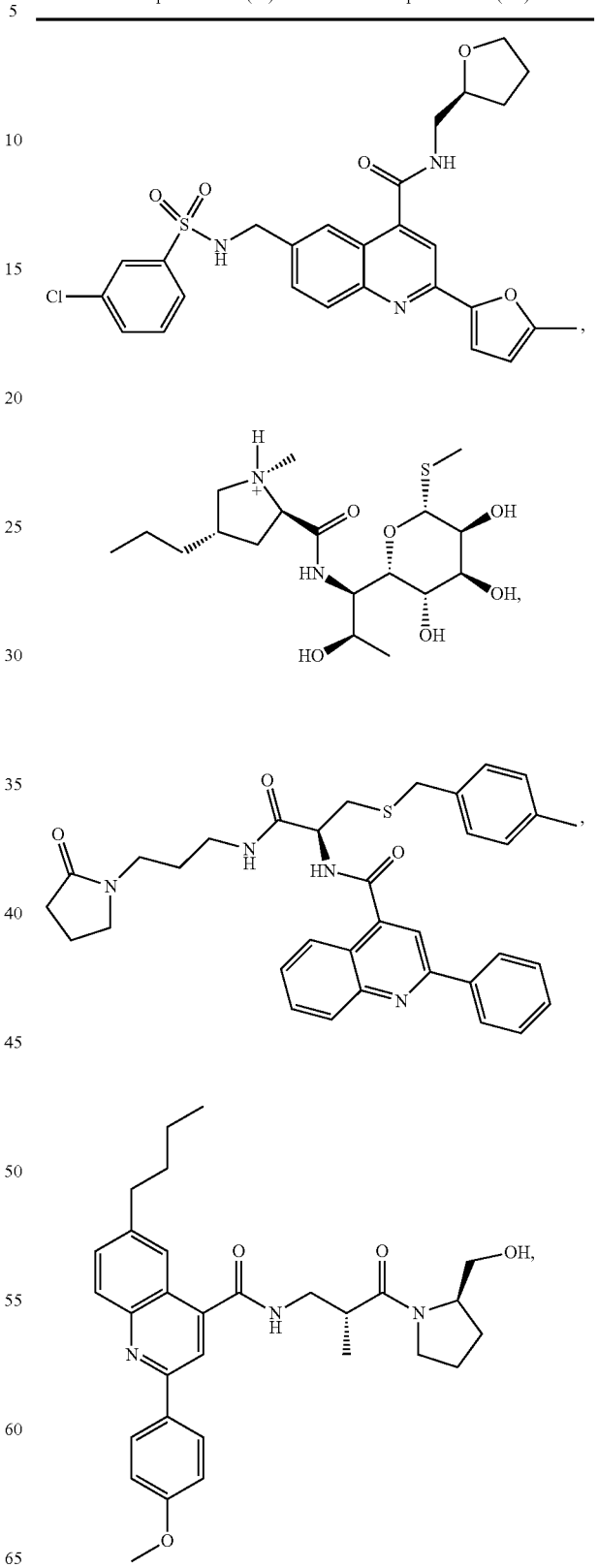

TABLE 1B-continued
Structures of the identified 19 compounds against immunoproteasome (IP) and constructive proteasome (CP).
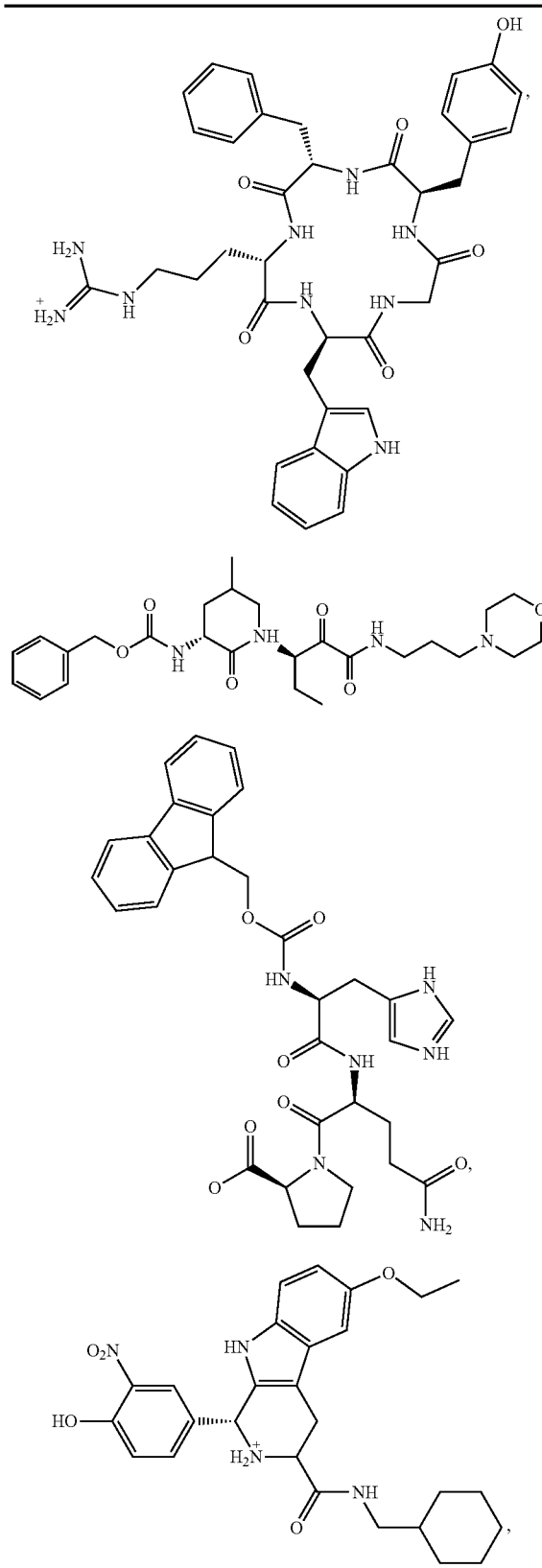
TABLE 1B-continued
Structures of the identified 19 compounds against immunoproteasome (IP) and constructive proteasome (CP).
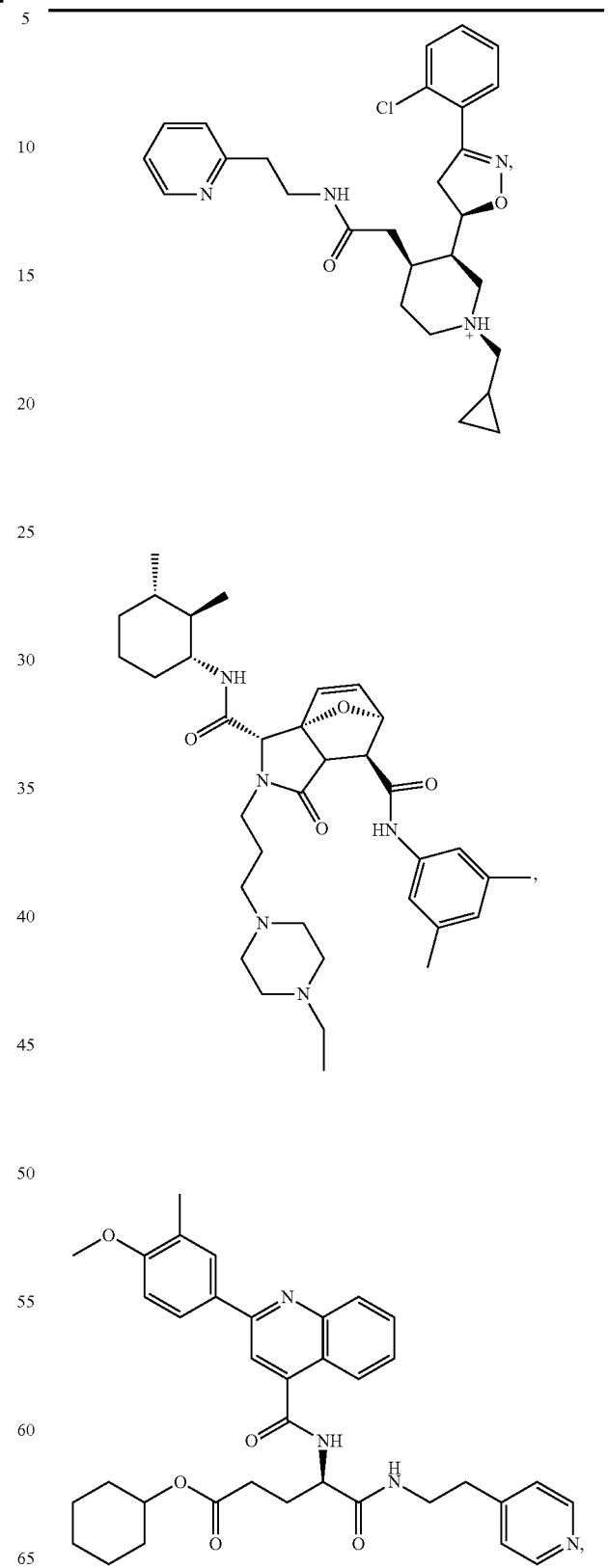

TABLE 1B-continued

Structures of the identified 19 compounds against immunoproteasome (IP) and constructive proteasome (CP).

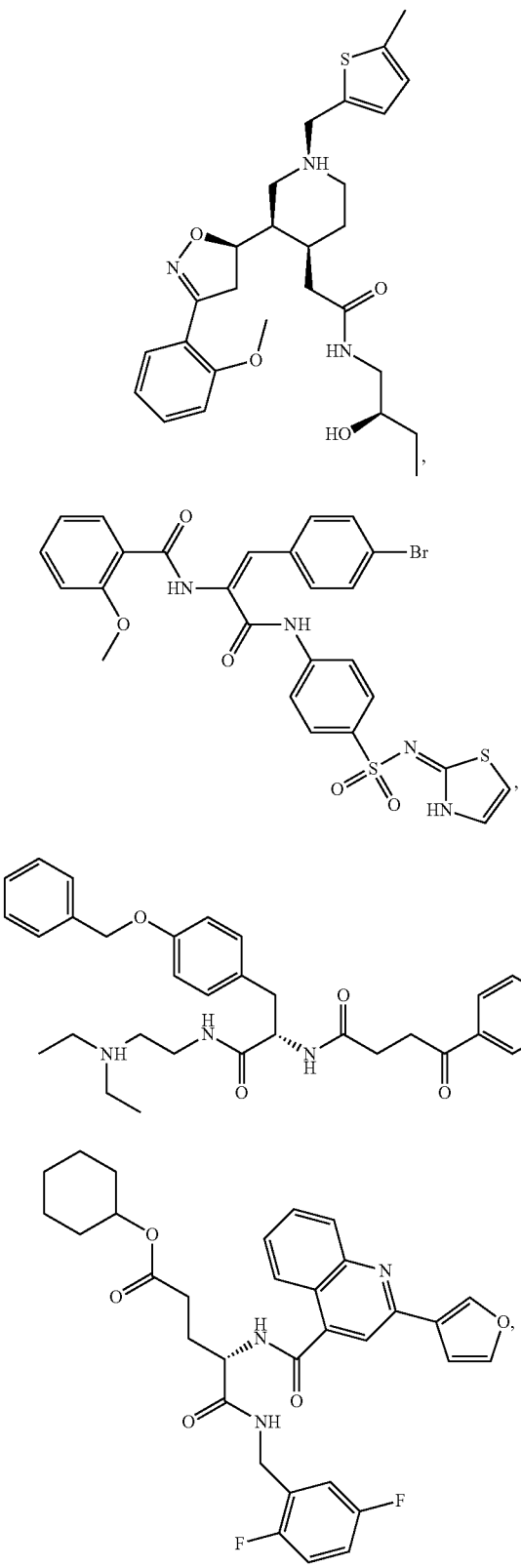

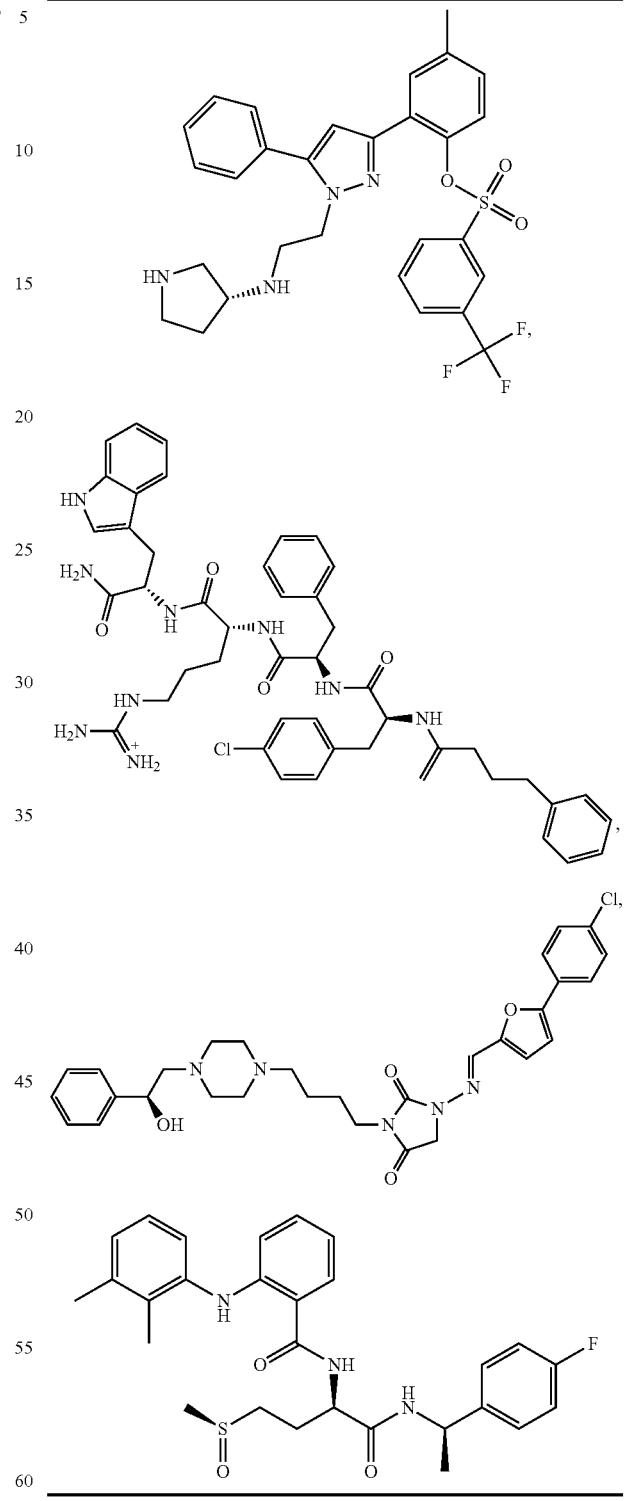

Immunoproteasome Binding

Figure 2A:
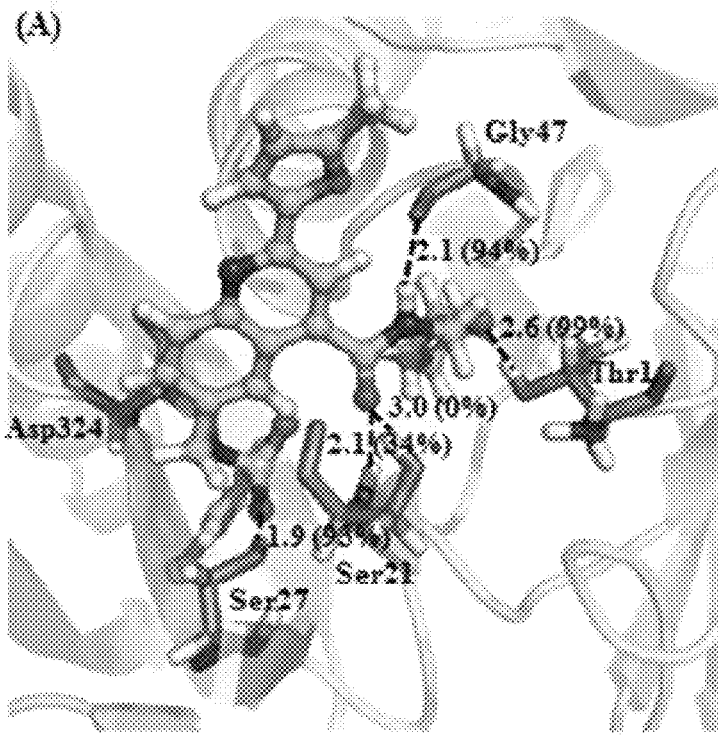
FIG. 2A and FIG. 2B. Binding structures of the immunoproteasome interacting with compounds 1 (FIG. 2A) and 3 (FIG. 2B). Indicated in the figures are the key distances (Å) of the protein-ligand interactions in the energy-minimized structures. Indicated in parentheses is the percent of the snapshots with the H . . . O distance shorter than 2.5 Å in the MD-simulated binding structure.
Figure 2B:
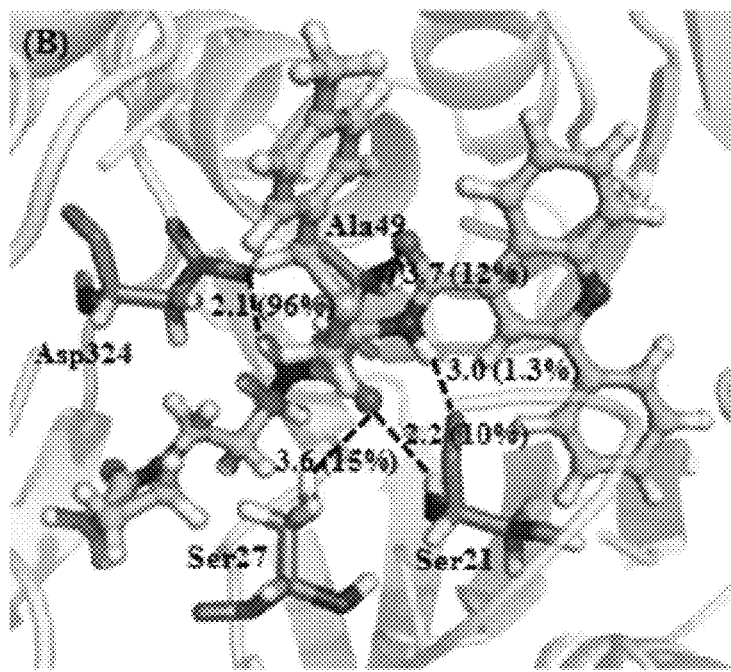

Depicted in FIG. 2A and FIG. 2B are the energy-minimized structures of the immunoproteasome binding with compounds 1 and 3. As shown in FIG. 2A, compound 1 has favorable hydrophilic interactions with amino-acid residues Thr1, Ser21, Ser27, and Gly47, including strong hydrogen bonds with the NH group of Ser21 backbone, hydroxyl group of Ser27 side chain, and carbonyl oxygen of Gly47 backbone. As shown in FIG. 2B, compound 3 has favorable hydrophilic interactions with Ser21, Ser27, Ala49, and Asp324, including hydrogen bonds with the NH group of Ser21 backbone and carboxylate oxygen of Asp324 side chain. Notably, the H . . . O distance with the hydroxyl oxygen of Ser27 side chain is as long as 3.6 Å in the energy-minimized structure.

Further, molecular dynamics (MD) simulation was carried out to examine the dynamically stable binding structures using the same computational protocol (starting from the energy-minimized structures) as used in previous computational studies on immunoproteasome-ligand binding.[10,11] For each inhibitor (compound 1 or 3) binding with immunoproteasome, a stable MD trajectory was obtained for 1 ns and 1000 snapshots were saved (one snapshot per ps) for structural analysis. Based on the MD trajectory with compound 3, the H . . . O distance with the hydroxyl oxygen of Ser27 side chain is shorter than 2.5 Å for ~15% of the snapshots. So, when 2.5 Å is used as the cutoff for the H . . . O distance in the hydrogen bonding, it can be said that the hydroxyl oxygen of Ser27 side chain has ~15% hydrogen bond with compound 3 (as indicated in FIG. 2B) and ~93% hydrogen bond with compound 1 (as indicated in FIG. 2A).

Notably, Ser21 and Ser27 are common residues of the immuno-proteasome that have favorable interactions with both compounds 1 and 3. Ser21 and Ser27 in the immuno-proteasome become Thr21 and Ala27, respectively, in the constitutive proteasome. The other residues of the immuno-proteasome interacting with compounds 1 and 3 are essentially the same as the corresponding ones of the constitutive proteasome. So, the selectivity of these new inhibitors for the immunoproteasome over the constitutive proteasome is likely associated with the favorable interaction between the inhibitors and the hydroxyl group of Ser27 side chain in the immunoproteasome. For the purpose of verification of this point, we also modeled constitutive proteasome binding with compounds 1 and 3 in the same way as we did for immunoproteasome with the same compounds, and we concluded that each compound binds with both proteins in the similar orientation, but without a hydrogen bond with Ala27 of constitutive proteasome (because Ala27 does not have a hydroxyl group on the side chain; data not shown).

Unlike currently available proteasome inhibitors in clinic, these new immunoproteasome inhibitors are non-peptide scaffold-based. In addition, these non-peptide scaffold-based compounds are contemplated to reversibly inhibit proteasomes due to the lack of reactive electrophilic pharmacophors.

The present inventors contemplated additional potent and selective inhibitors designed to enhance the favorable interactions with all of the amino-acid residues mentioned above. Particularly, enhancement of the favorable interaction with Ser27 of the immunoproteasome is expected to improve both the potency and selectivity of the immunoproteasome inhibitors.

The present inventors contemplate unique compounds that make use of the non-peptide scaffolds of the 19 exemplary compounds identified in this Example. Such compounds can be synthesized and tested to improve the inhibitory activity and selectivity. Thus, the present inventors contemplate use of compounds including these non-peptide scaffolds as immunoproteasome inhibitors for use as therapeutic agents.

Inhibitory Activity

Unique candidate inhibitors were synthesized and tested for their inhibitory activity. The tested candidate inhibitors are set forth in Table 2, Table 3, and Table 4.

TABLE 2

| Compound ID | R |
| --- | --- |
| D2 | 3-chlorophenylsulfonyl |
| D2-1 | 3-chlorobenzoyl |
| D2-2 | 2,3-dihydro-1,4-benzodioxin-6-ylsulfonyl |
| D2-5 | furan-2-carbonyl |
| D2-6 | acetyl |
| D2-10 | morpholinoacetyl |
| D2-12 | benzyloxycarbonyl |

TABLE 2-continued

[Structure: quinoline core with 4-carboxamide linked to NH-CH2-(tetrahydrofuran-2-yl), 2-(5-methylfuran-2-yl), and 6-CH2-NH-R substituent]

| Compound ID | R |
|---|---|
| D2-15 | 2,3-dihydro-1,4-benzodioxin-6-yl-C(=O)-CH< |
| D2-16 | 4-chlorophenyl-CH2-C(=O)-CH< |
| D2-19 | CH3-CH2-O-CH2-CH2-C(=O)-CH< |
| D2-20 | naphthalen-2-yl-CH2-C(=O)-CH< |
| D2-22 | H3N(+)-CH< |
| D2-32 | 3-(trifluoromethyl)phenyl-C(=O)-CH< |
| D2-33 | 3-fluorophenyl-C(=O)-CH< |
| D2-34 | 3-bromophenyl-C(=O)-CH< |
| D2-35 | 3-methylphenyl-C(=O)-CH< |
| D2-36 | 3-(methoxycarbonyl)phenyl-C(=O)-CH< |
| D2-37 | 4-chlorophenyl-C(=O)-CH< |
| D2-38 | 3,5-dichlorophenyl-C(=O)-CH< |
| D2-39 | 1,3-benzodioxol-5-yl-C(=O)-CH< |
| D2-40 | 3-chloro-4-methoxyphenyl-C(=O)-CH< |
| D2-41 | 3-chlorophenyl-CH2-C(=O)-CH< |

TABLE 2-continued
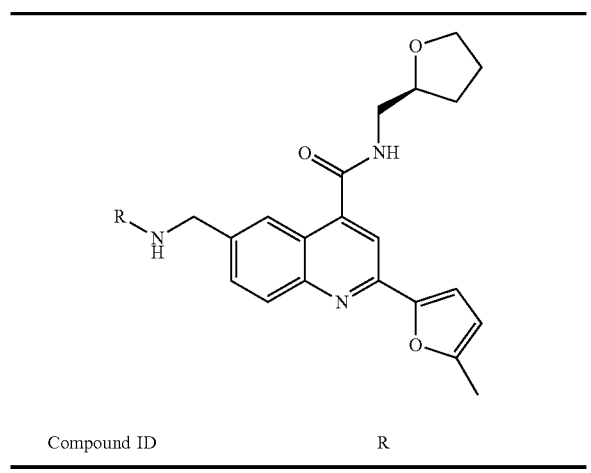
| Compound ID | R |
|---|---|
| D2-42 | 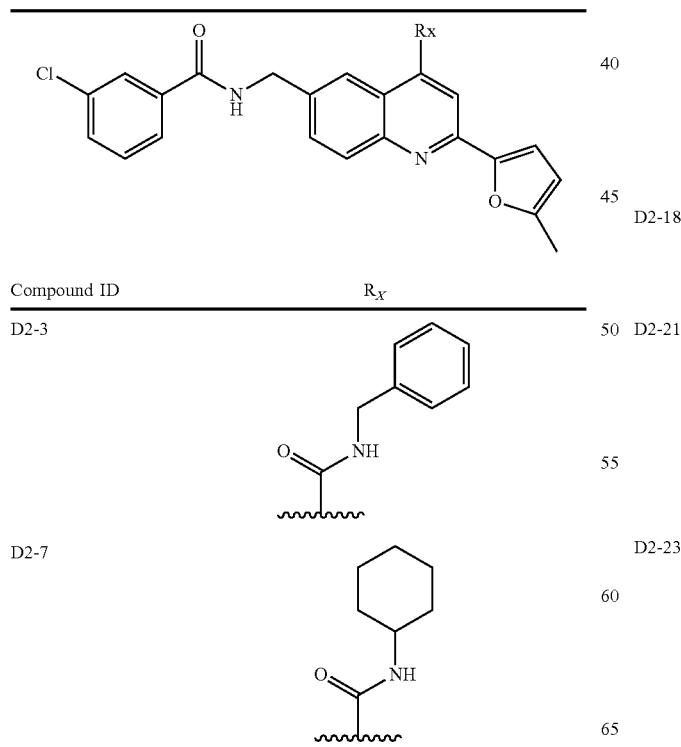 |
| D2-43 | |
TABLE 3
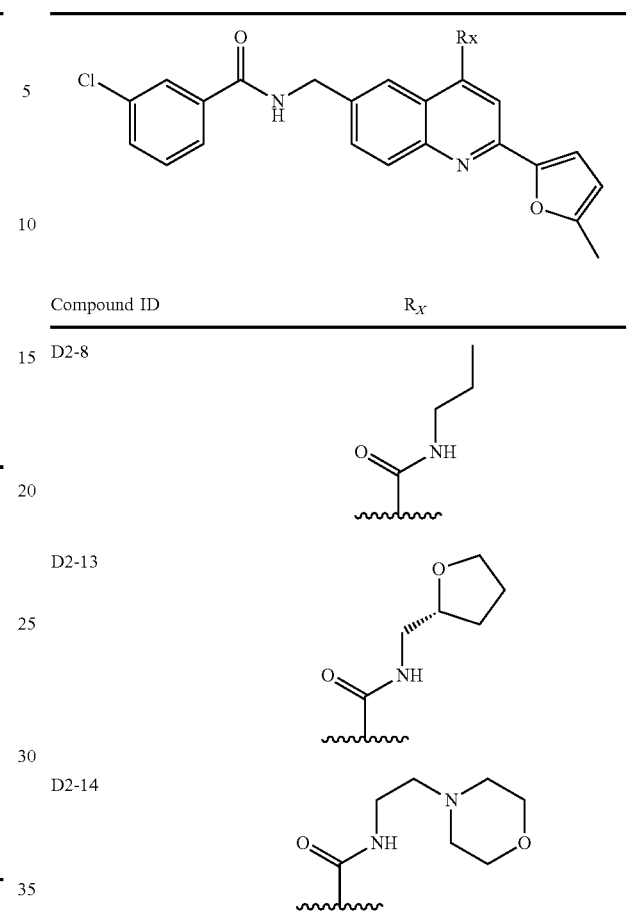
| Compound ID | $R_X$ |
|---|---|
| D2-3 | (benzyl amide) |
| D2-7 | (cyclohexyl amide) |
| D2-8 | (n-propyl amide) |
| D2-13 | (tetrahydrofuran-2-ylmethyl amide) |
| D2-14 | (2-morpholinoethyl amide) |
| D2-17 | (3-(2-oxopyrrolidin-1-yl)propyl amide) |
| D2-18 | (carboxymethyl amide) |
| D2-21 | (1-hydroxy-2-methylpropan-2-yl amide) |
| D2-23 | (cyclohexylmethyl amide) |

TABLE 3-continued

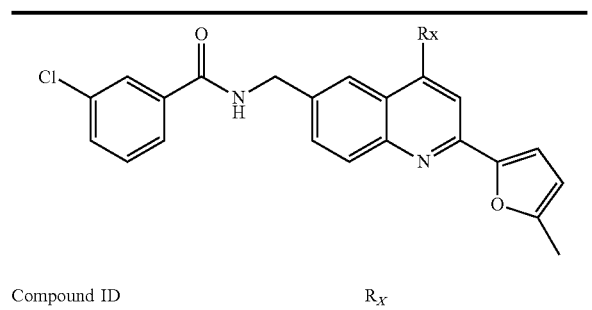

| Compound ID | $R_X$ |
|---|---|
| D2-24 | pyrazin-2-ylmethyl-aminocarbonyl group |
| D2-25 | (1-benzyloxycarbonyl-pyrrolidin-3-yl)methyl-aminocarbonyl group |
| D2-26 | (pyrrolidin-3-yl-ammonium)methyl-aminocarbonyl group |
| D2-27 | 4-chlorobenzyl-aminocarbonyl group |
| D2-28 | 2-ammonioethyl-aminocarbonyl group |
| D2-29 | 1-(6-methoxynaphthalen-2-yl)ethyl-aminocarbonyl group |

TABLE 3-continued

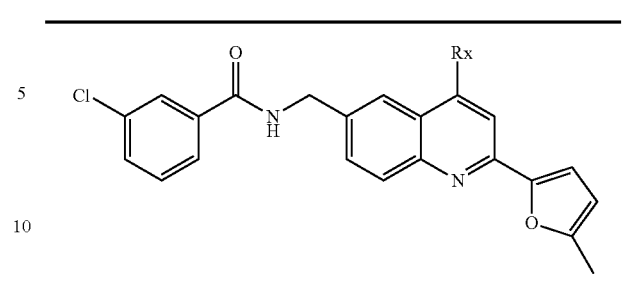

| Compound ID | $R_X$ |
|---|---|
| D2-30 | benzyl (2S)-2-aminocarbonylamino-3-(1H-indol-3-yl)propanoate group |
| D2-31 | (2S)-2-aminocarbonylamino-3-(1H-indol-3-yl)propanoate group |
| D2-44 | (1-Boc-pyrrolidin-2-yl)methyl-aminocarbonyl group |
| D2-45 | (1-Fmoc-piperidin-4-yl)methyl-aminocarbonyl group |
| D2-46 | (pyrrolidin-2-yl)methyl-aminocarbonyl group |

TABLE 3-continued

| Compound ID | $R_X$ |
|---|---|
| D2-47 | (3-piperidinyl)methyl-NH-C(O)- |
| D2-48 | (1-Boc-3-pyrrolidinyl)methyl-NH-C(O)- |
| D2-49 | (1-Boc-3-pyrrolidinyl)methyl-NH-C(O)- |
| D2-50 | (1-Boc-3-piperidinyl)methyl-NH-C(O)- |
| D2-51 | (3-pyrrolidinyl)methyl-NH-C(O)- |
| D2-52 | ((S)-1-methyl-3-pyrrolidinyl)methyl-NH-C(O)- |

TABLE 4

| Compound ID | $R_X$ |
|---|---|
| D2-1 | 5-methyl-2-furyl |
| D2-4 | 2,3-dihydrobenzofuran-5-yl |
| D2-9 | phenyl |
| D2-11 | CH₃ (methyl via CH) |

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Goldberg, A. L. Nature 2003, 426, 895.
2. Kisselev, A. F.; Goldberg, A. L. Chem. Biol. 2001, 8, 739.
3. McBride, A.; Ryan, P. Y. Expert Rev. Anticancer Ther. 2013, 13, 339.
4. Chen, D.; Frezza, M.; Schmitt, S.; Kanwar, J.; Dou, Q. P. Cur. Cancer Drug Targets 2011, 11, 239.
5. Richardson, P. G.; Barlogie, B.; Berenson, J.; Singhal, S.; Jagannath, S.; Irwin, D.; Rajkumar, S. V.; Srkalovic, G.; Alsina, M.; Alexanian, R.; Siegel, D.; Orlowski, R. Z.; Kuter, D.; Limentani, S. A.; Lee, S.; Hideshima, T.; Esseltine, D. L.; Kauffman, M.; Adams, J.; Schenkein, D. P.; Anderson, K. C. N. Engl. J. Med. 2003, 348, 2609.
6. Siegel, D. S.; Martin, T.; Wang, M.; Vij, R.; Jakubowiak, A. J.; Lonial, S.; Trudel, S.; Kukreti, V.; Bahlis, N.; Alsina, M.; Chanan-Khan, A.; Buadi, F.; Reu, F. J.; Somlo, G.; Zonder, J.; Song, K.; Stewart, A. K.; Stadtmauer, E.; Kunkel, L.; Wear, S.; Wong, A. F.; Orlowski, R. Z.; Jagannath, S. Blood 2012.
7. Rock, K. L.; Goldberg, A. L. Annu. Rev. Immunol. 1999, 17, 739.
8. Parlati, F.; Lee, S. J.; Aujay, M.; Suzuki, E.; Levitsky, K.; Lorens, J. B.; Micklem, D. R.; Ruurs, P.; Sylvain, C.; Lu, Y.; Shenk, K. D.; Bennett, M. K. Blood 2009, 114, 3439.
9. Vlieghe, P.; Lisowski, V.; Martinez, J.; Khrestchatisky, M. Drug Discovery Today 2010, 15, 40.
10. Lei, B.; Abdul Hameed, M. D. M.; Hamza, A.; Wehenkel, M.; Muzyka, J. L.; Yao, X.-J.; Kim, K.-B.; Zhan, C.-G. J. Phys. Chem. B 2010, 114, 12333.
11. Lei, B.; Hamza, A.; Zhan, C.-G. Theor. Chem. Acc. 2012, 131, 1203.
12. Wei, D.; Lei, B.; Tang, M.; Zhan, C.-G. J. Am. Chem. Soc. 2012, 134, 10436.
13. Yang, W.; AbdulHameed, M. D. M.; Hamza, A.; Zhan, C.-G. Bioorg. Med. Chem. Lett. 2012, 22, 1629.
14. Hamza, A.; Zhao, X.; Tong, M.; Tai, H. H.; Zhan, C. G. Bioorg. Med. Chem. 2011, 19, 6077.
15. McGann, M. R.; Almond, H. R.; Nicholls, A.; Grant, J. A.; Brown, F. K. Biopolymers 2003, 68, 76.
16. Case, D. A.; Cheatham, T. E.; Darden, T.; Gohlke, H.; Luo, R.; Merz, K. M.; Onufriev, A.; Simmerling, C.; Wang, B.; Woods, R. J. J. Comput. Chem. 2005, 26, 1668.
17. Ho, Y. K.; Bargagna-Mohan, P.; Wehenkel, M.; Mohan, R.; Kim, K.-B. Chem. Biol. 2007, 14, 419.
18. Kisselev, A. F.; Goldberg, A. L. Methods Enzymol. 2005, 398, 364.
19. Naim, M.; Bhat, S.; Rankin, K. N.; Dennis, S.; Chowdhury, S. F.; Siddiqi, I.; Drabik, P.; Sulea, T.; Bayly, C. I.; Jakalian, A.; Purisima, E. O. J. Chem. Inf. Model. 2007, 47, 122.
20. Kasam, V.; Lee, N. R.; Kim, K. B.; Zhan, C. G. Bioorg Med Chem Lett. 2014, 24(15): 3614-7.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound, having the formula of:

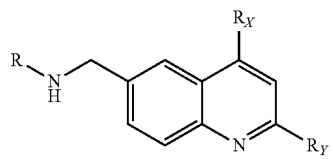

wherein,

R is selected from the group consisting of

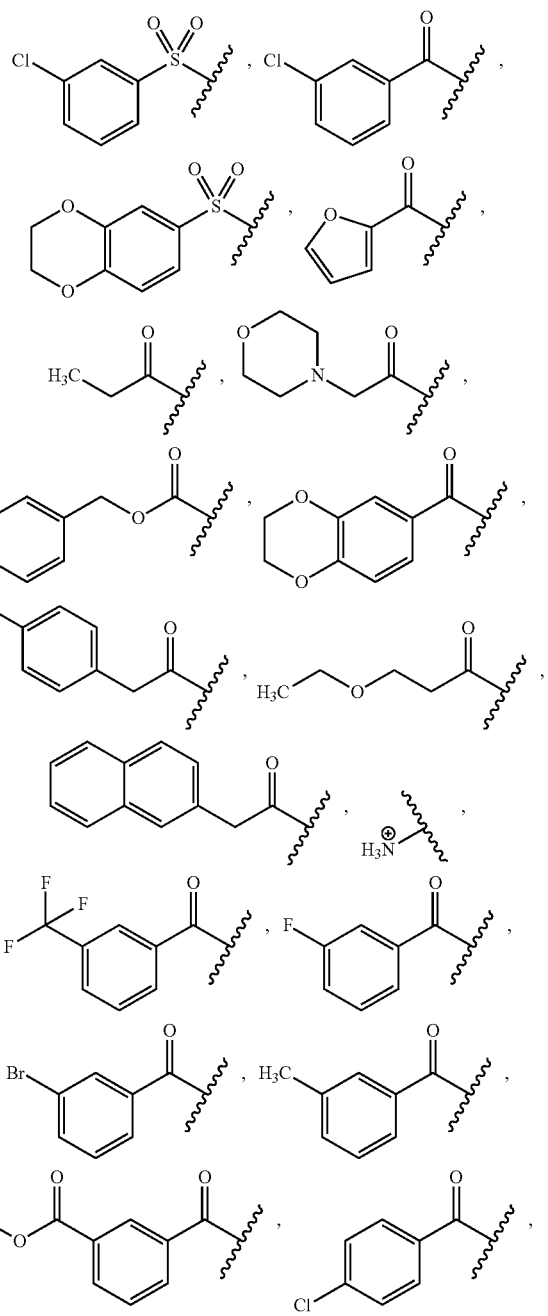

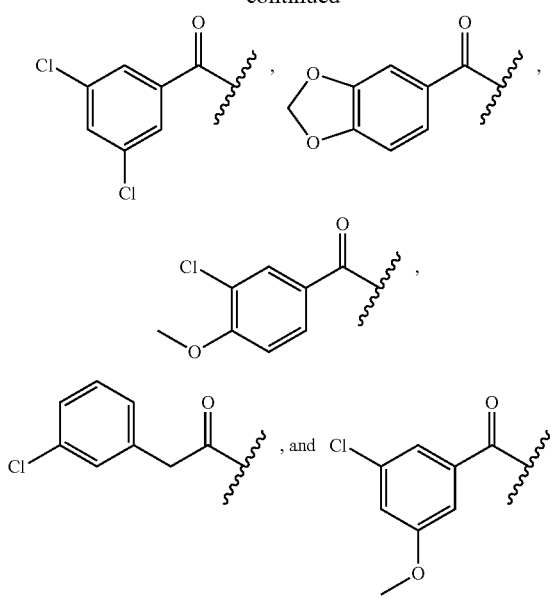
$R_X$ is selected from the group consisting of
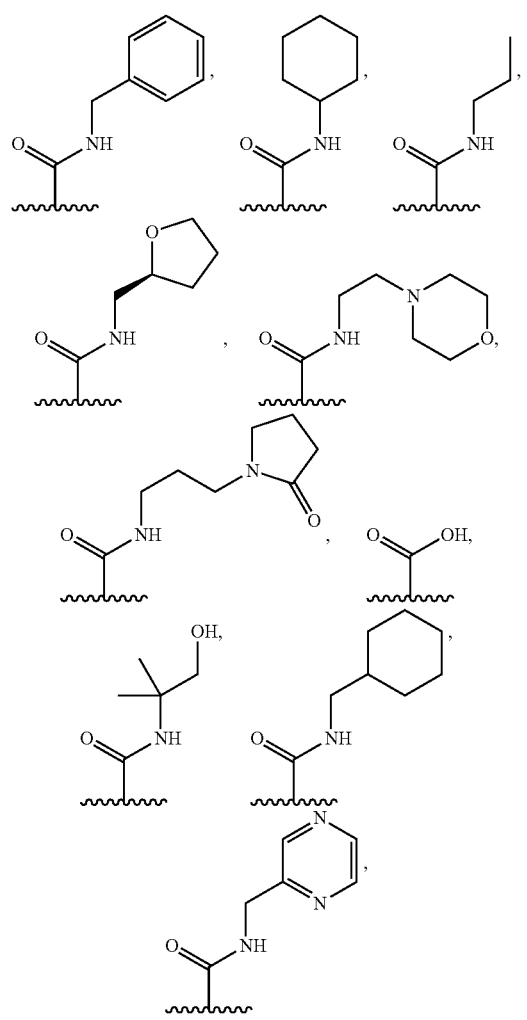
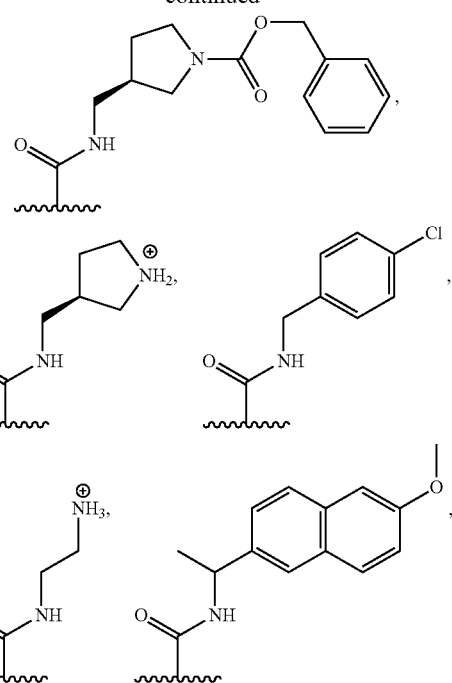

-continued
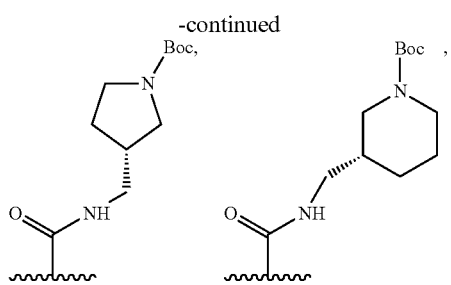
, and
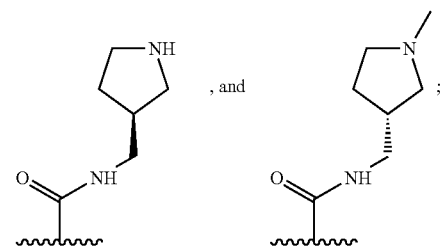 [SMILES: *C(=O)NC[C@H]1CCNC1 ; *C(=O)NC[C@@H]1CCN(C)C1]
;
$R_Y$ is selected from the group consisting of
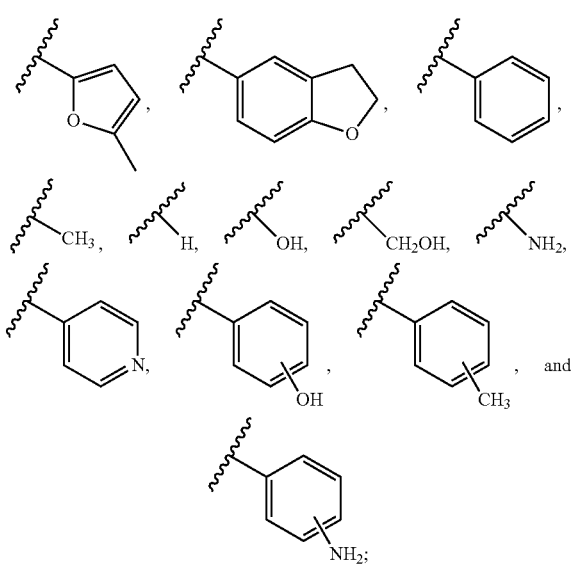
with the proviso that if R is
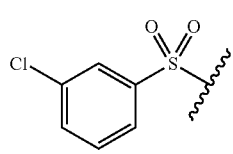 [SMILES: *S(=O)(=O)c1cccc(Cl)c1]
and $R_Y$ is
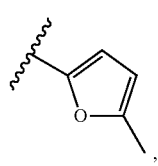 [SMILES: *c1ccc(C)o1]
then $R_X$ is not
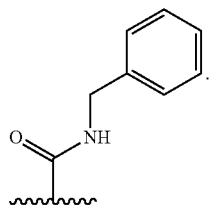 [SMILES: *C(=O)NCc1ccccc1]
.
2. The compound of claim 1, wherein $R_Y$ is
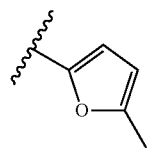
.
3. The compound of claim 1, having the formula of
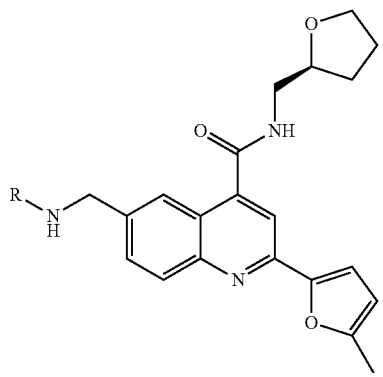
wherein R is selected from the group consisting of
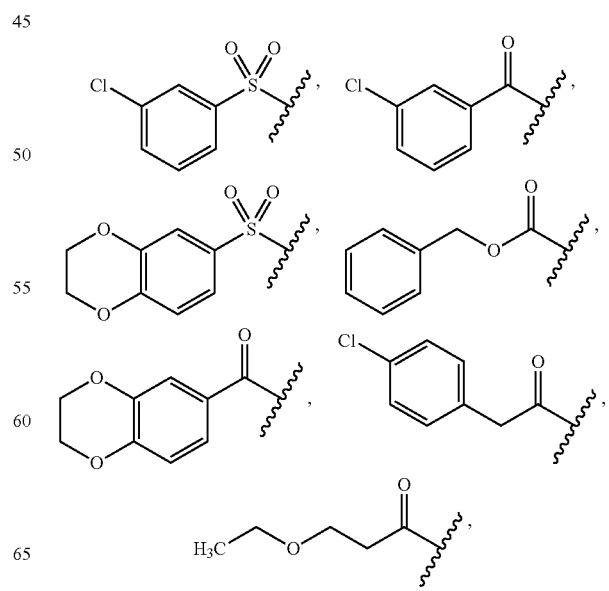

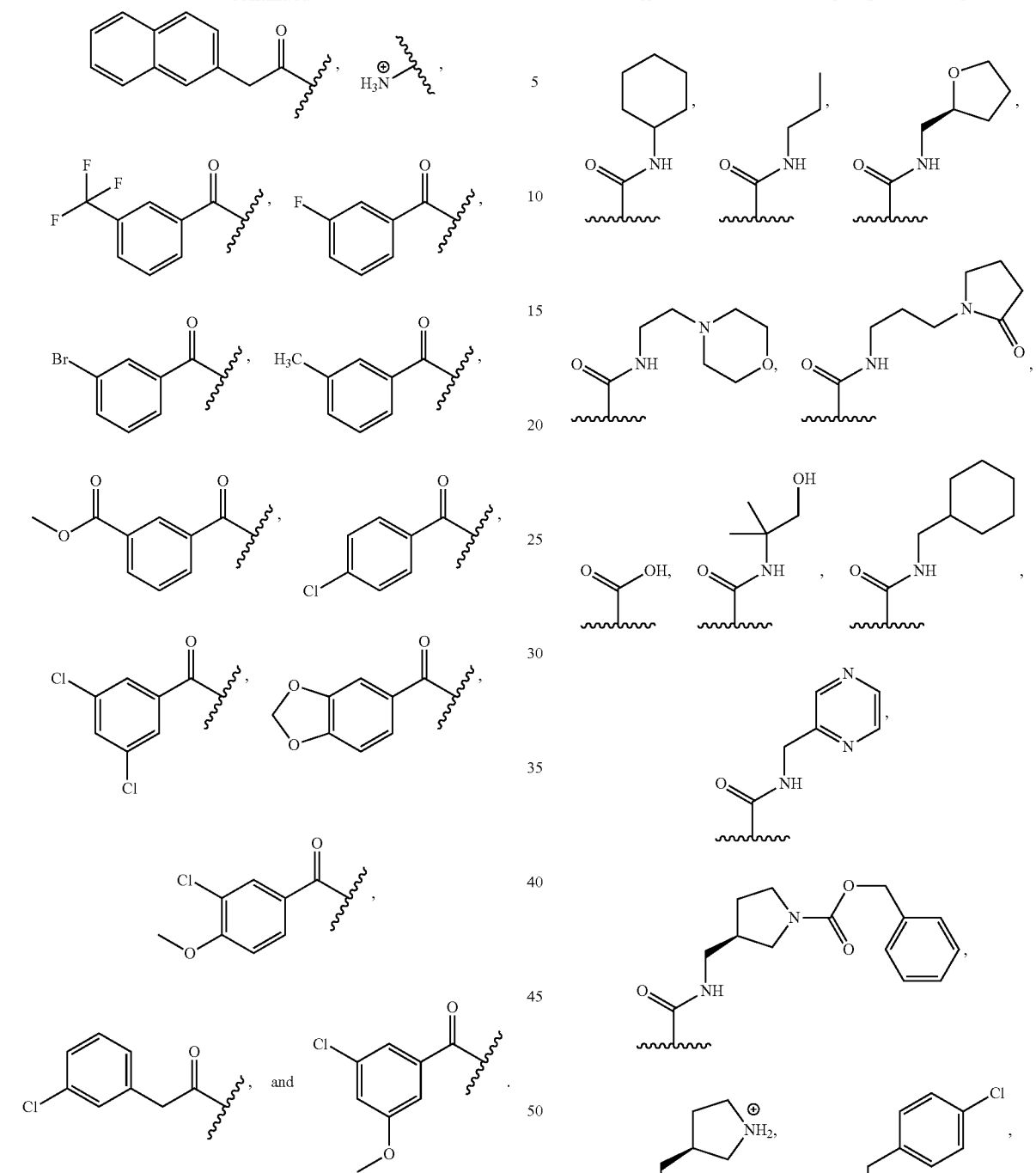
4. The compound of claim 1, having the formula of
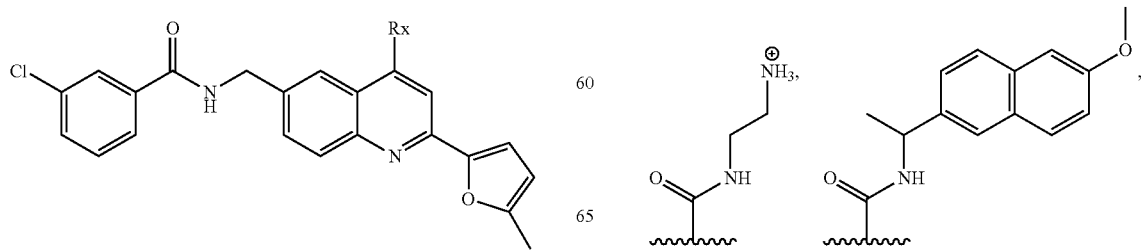
wherein $R_X$ is selected from the group consisting of -continued
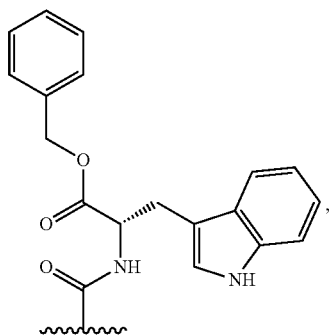
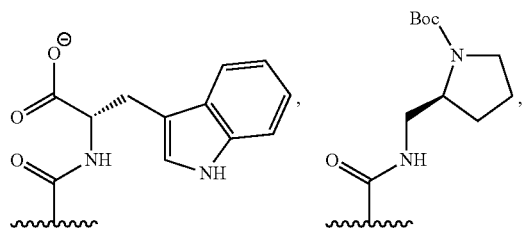
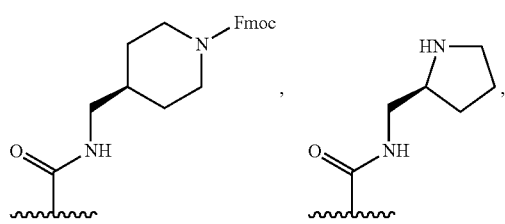
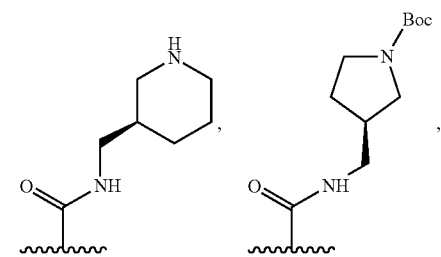
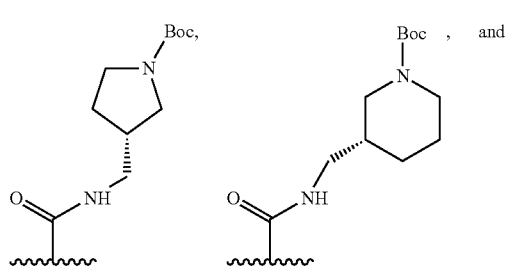
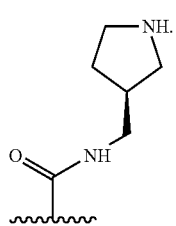
5. The compound of claim 1, having the formula of
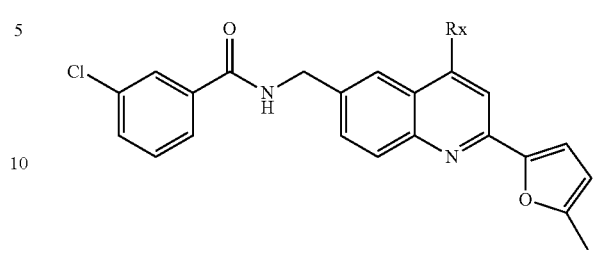
wherein $R_X$ is selected from the group consisting of
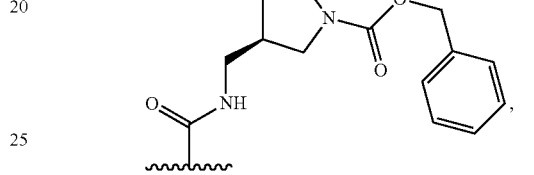
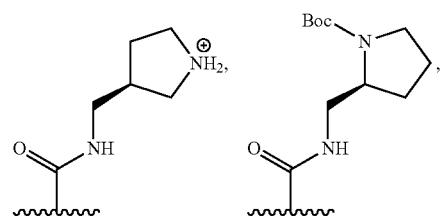
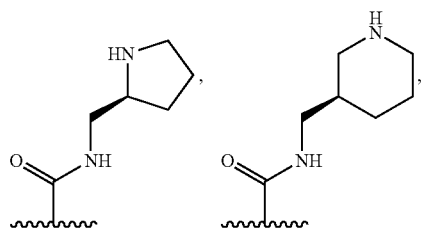
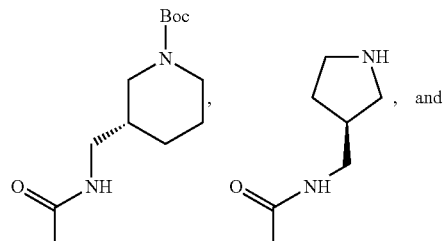
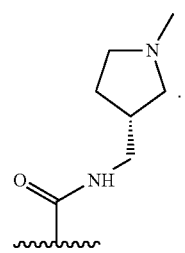

6. The compound of claim 5, wherein $R_X$ is selected from

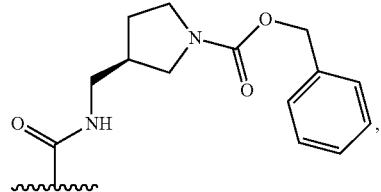

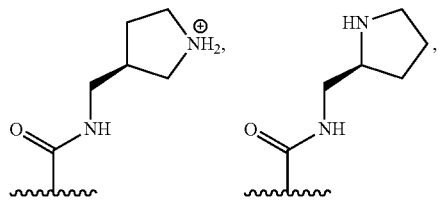

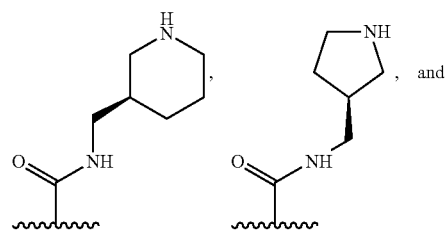, and

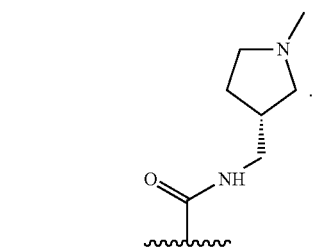

7. The compound of claim 5, wherein $R_X$ is

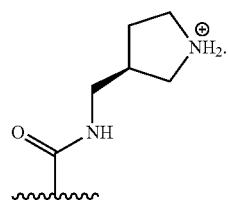

8. The compound of claim 5, wherein $R_X$ is

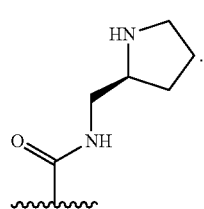 [SMILES: *C(=O)NC[C@@H]1CCCN1]

9. The compound of claim 5, wherein $R_X$ is

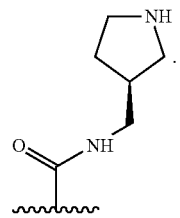 [SMILES: *C(=O)NC[C@H]1CCNC1]

10. The compound of claim 5, wherein $R_X$ is

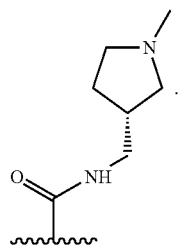 [SMILES: *C(=O)NC[C@@H]1CCN(C)C1]

11. A pharmaceutical composition for use in inhibiting immunoproteasome activity, comprising a compound according to claim 1, or a pharmaceutically-acceptable salt thereof, and a pharmaceutically-acceptable carrier or excipient.

12. A compound having a formula selected from the group consisting of:

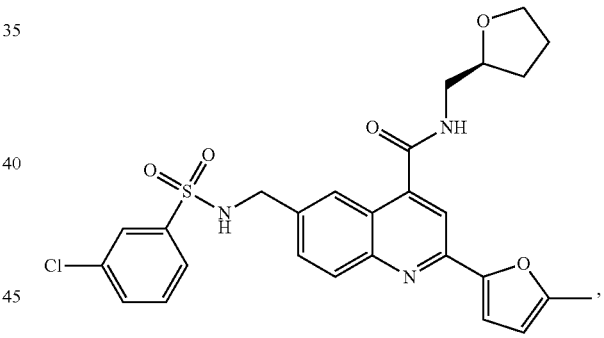

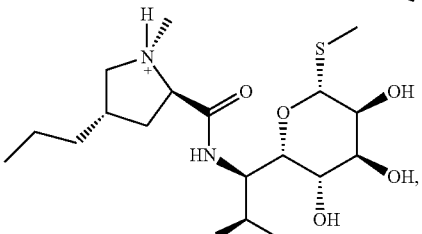

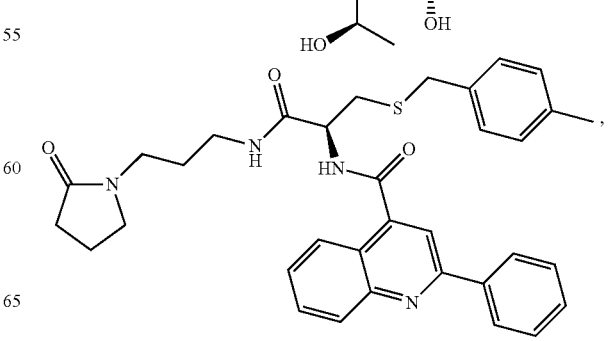

55
-continued
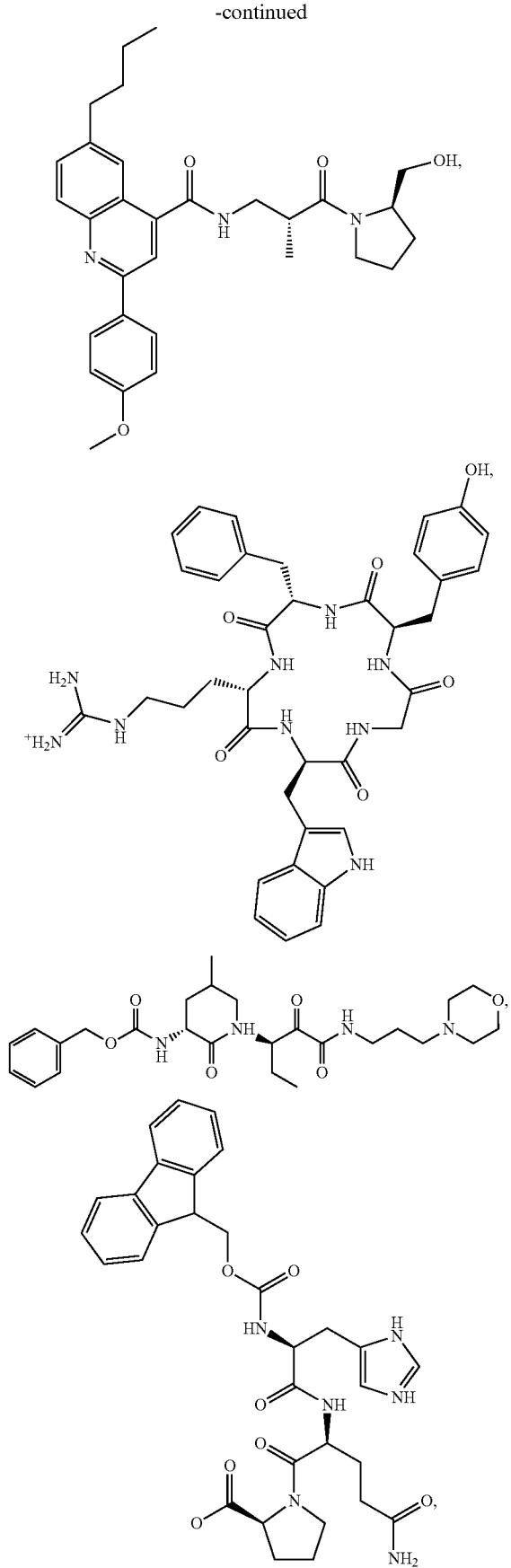
56
-continued
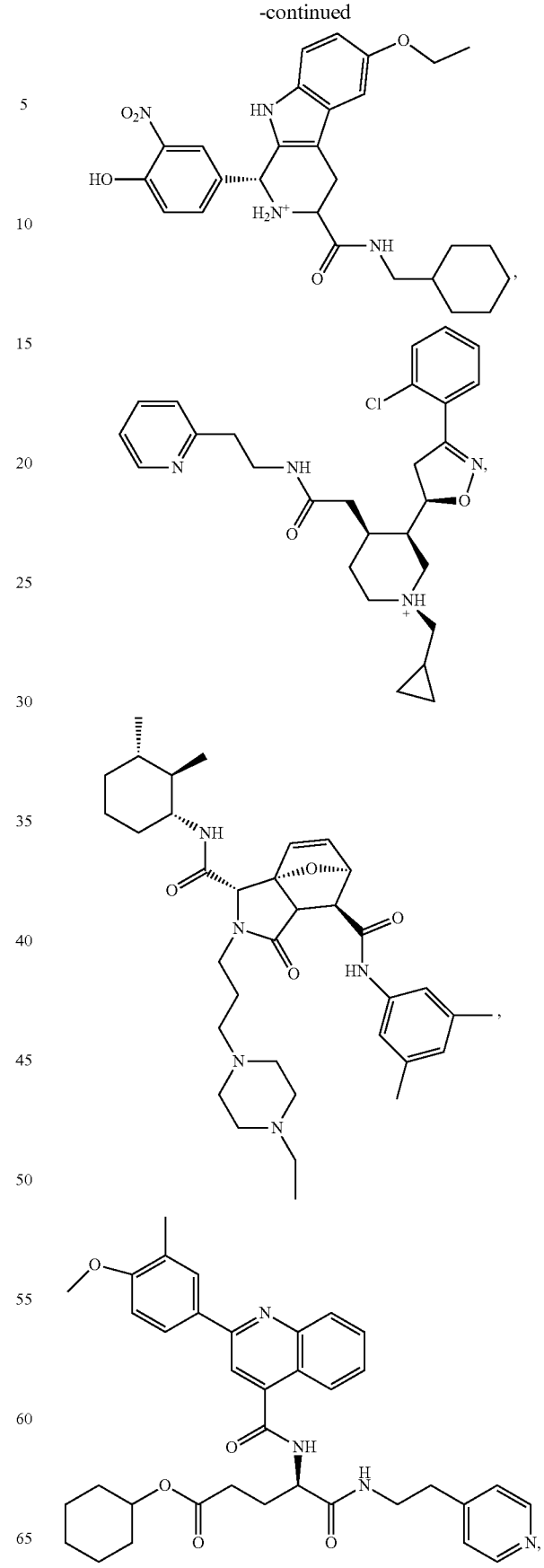

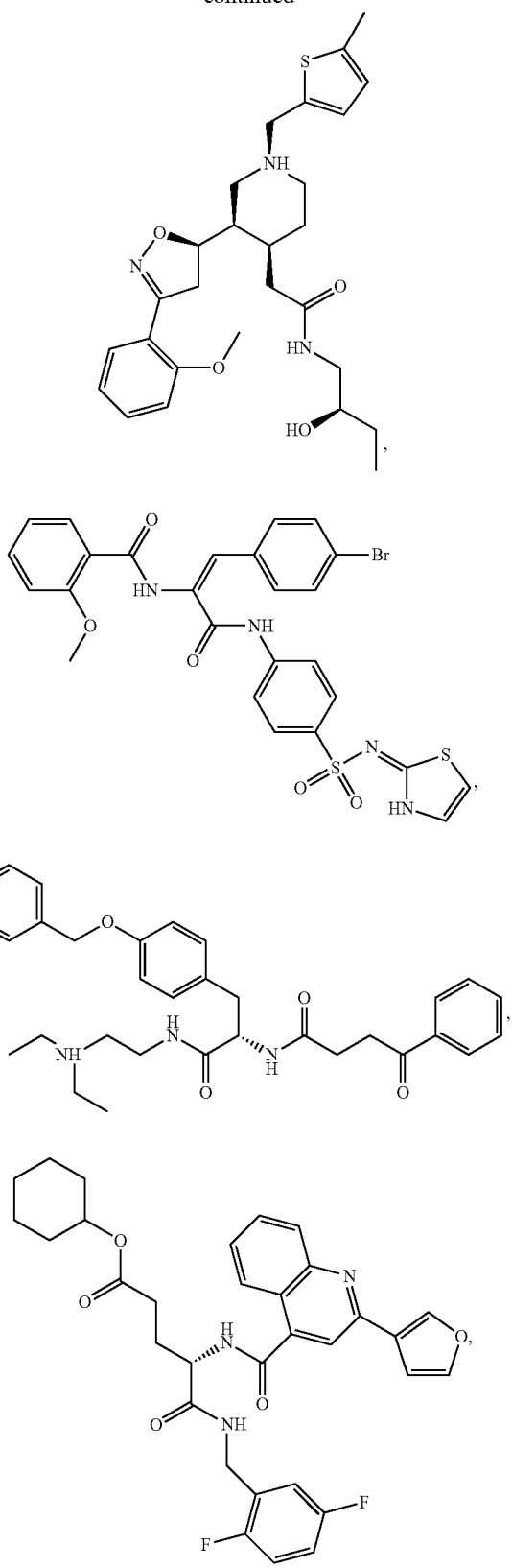
13. A pharmaceutical composition for use in inhibiting immunoproteasome activity, comprising a compound according to claim 12, or a pharmaceutically-acceptable salt thereof, and a pharmaceutically-acceptable carrier or excipient.
* * * * *